United States Patent
Kao et al.

(10) Patent No.: US 7,794,469 B2
(45) Date of Patent: Sep. 14, 2010

(54) ADJUSTABLE UNIVERSAL SURGICAL PLATFORM

(75) Inventors: Changquing C. Kao, Brentwood, TN (US); J. Michael Fitzpatrick, Nashville, TN (US); Robert F. Labadie, Nashville, TN (US); Peter E. Konrad, Old Hickory, TN (US)

(73) Assignee: Vanderbilt University, Nashville, TN (US)

( * ) Notice: Subject to any disclaimer, the term of this patent is extended or adjusted under 35 U.S.C. 154(b) by 744 days.

(21) Appl. No.: 11/594,700

(22) Filed: Nov. 7, 2006

(65) Prior Publication Data

US 2007/0106305 A1 May 10, 2007

Related U.S. Application Data

(60) Provisional application No. 60/734,052, filed on Nov. 7, 2005.

(51) Int. Cl.
 *A61B 19/00* (2006.01)
(52) U.S. Cl. .................................................... 606/130
(58) Field of Classification Search ................. 600/415, 600/417, 424, 429; 606/108, 129, 130; 248/177.1, 248/181.1, 166, 170, 188.7
See application file for complete search history.

(56) References Cited

U.S. PATENT DOCUMENTS

| | | | | |
|---|---|---|---|---|
| 3,881,675 A * | 5/1975 | Matchett | ...................... | 248/170 |
| 4,366,940 A * | 1/1983 | Vargas | ......................... | 248/542 |
| 5,637,074 A * | 6/1997 | Andino et al. | ................. | 600/29 |
| 5,749,549 A * | 5/1998 | Ashjaee | ...................... | 248/168 |
| 5,752,962 A | 5/1998 | D'Urso | | |
| 5,810,712 A * | 9/1998 | Dunn | .......................... | 600/114 |
| 5,903,995 A * | 5/1999 | Brubach | ......................... | 42/94 |
| 6,471,711 B2 * | 10/2002 | Irie et al. | ..................... | 606/130 |
| 6,579,281 B2 * | 6/2003 | Palmer et al. | .................. | 606/1 |
| 6,843,015 B2 * | 1/2005 | Sharp | ............................ | 42/94 |
| 2002/0169460 A1 | 11/2002 | Foster et al. | | |
| 2005/0070781 A1 * | 3/2005 | Dawant et al. | .............. | 600/407 |

* cited by examiner

*Primary Examiner*—(Jackie) Tan-Uyen T Ho
*Assistant Examiner*—Thomas McEvoy
(74) *Attorney, Agent, or Firm*—Morris Manning Martin LLP; Tim Tingkang Xia, Esq.

(57) ABSTRACT

A surgical platform usable for performing a surgical procedure. In one embodiment, the surgical platform comprises a base portion configured to receive at least one probe; a plurality of adjustable legs configured to support the base portion, each adjustable legs having a first end portion and an opposite, second end potion defining a length therebetween; and at least one movable portion configured to adjust the length of at least one adjustable leg.

15 Claims, 23 Drawing Sheets

ADJUSTABLE UNIVERSAL SURGICAL PLATFORM

CROSS-REFERENCE TO RELATED PATENT APPLICATION

This application claims the benefit, pursuant to 35 U.S.C. §119(e), of U.S. provisional patent application Ser. No. 60/734,052, filed Nov. 7, 2005, entitled "ADJUSTABLE UNIVERSAL SURGICAL PLATFORM," by Changquing C. Kao, J. Michael Fitzpatrick, Robert F. Labadie and Peter E. Konrad, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

STATEMENT OF FEDERALLY-SPONSORED RESEARCH

This invention was made in part with U.S. Government support under Grant R21CA133477, awarded by the National Institute of Health. The U.S. Government has certain rights in this invention.

FIELD OF THE INVENTION

The present invention generally relates to a surgical platform. More particularly, the present invention relates to a surgical platform that has a plurality of adjustable legs.

BACKGROUND OF THE INVENTION

Stereotactic neurosurgery is a field of neurosurgery in which a probe is advanced through a burr hole to a target of interest by means of a mechanical device attached to the skull with aiming based on pre-operative images. The probe may be a biopsy needle or an implantable device, but it is geometrically rigid, so that its tip can be brought to a target of interest specified on a pre-operative image, by means of a geometrical calculation. For the past decade, the field has been advancing from the imposition of large, classical metal frames, which encompass the entire head of a patient, to the attachment of small platforms placed only over an entry site to reduce patient discomfort, facilitate surgical access, allow multiple targeting during one surgery via multiple platforms, and reduce procedure time, while maintaining the same level of accuracy.

Classical metal frames are designed for approaching one target at a time with an unrestricted entry point towards the deep target by employing the principle that the target is at the center of a sphere. Because of the long trajectories, both accuracy and patient comfort are challenged by the demands of surgeries for deep brain stimulation (DBS) in which the patients are awake throughout the lengthy surgery procedure (about 5-8 hours).

During the last few years, microplatforms, such as a NEXFRAME™ (Image-Guided Neurologics, Inc, Melbourne, Fla.) and a microTargeting® platform (FHC Inc, Bowdoinham, Me.), also known as a STarFix™ platform, have become available as replacements for the classical frames for DBS stereotactic surgery.

It is understood that the NEXFRAME™ platform requires the attachment of bone-implanted fiducials, the subsequent acquisition of a preoperative tomogram, and intraoperative optical tracking to aim a probe at its target. However, there are problems regarding geometrically stability, limited space for access to the burr hole and surgical manipulation once the tower is mounted, the time consuming process of aiming, and the difficulty of locking on the target. Access to the burr hole is crucially important for the purpose of stopping bleeding from the bone cavity, dura, and the surface of the cortex during the procedure. Aiming is achieved by watching a guiding icon on the screen of the intraoperative tracking system, while adjusting the orientation of the platform. When the icon indicates a correct trajectory, the platform must be locked into place with one hand, while it is held at the correct trajectory with the other. The trajectory is two-dimensional, meaning that there are two mutually perpendicular angular adjustments required, each of which must be set simultaneously for the correct trajectory. Finding the correct trajectory via the guiding icon is time consuming because of the difficulty of making fine adjustments of one angle of the approach without changing the other angle. A further difficulty with this aiming procedure is maintaining both angles of the correct trajectory while locking the device on target. The locking step can be especially frustrating, because, if either angle is changed inadvertently during locking, as revealed by the guiding icon, the device must be unlocked and the adjustment started from the beginning. Typically several iterations are required, resulting in wasted operating time.

It is understood the other alternative, the STarFix™, also requires the attachment of bone-implanted fiducials and the subsequent acquisition of a preoperative tomogram, but it does not require intraoperative optical tracking for aiming. Instead the STarFix™ is custom made for each patient based on a pre-operative tomogram and the surgeon's identification of the entry point and the target on that tomogram. The device arrives at the operating suite pre-aimed with no adjustment required intraoperatively. It is a one-piece rigid plastic block having a cylindrical hole that accommodates the probe, supported by a plurality of legs, each of which attaches to a base that is implanted in the skull. Fiducial markers are attached to these same bases before the pre-operative image is acquired and discarded after imaging. The shape of the STarFix™ provides far greater access to the burr hole, but its paramount advantage is that it is "pre-aimed", obviating the aiming procedure required by the NEXFRAME™. An additional benefit, but one that does not directly affect accuracy or operating time is that the expense of an intraoperative tracking system is avoided. One of its disadvantages relative to the NEXFRAME™ is that the patient must wait between the acquisition of the tomogram and the delivery of the STarFix™. Currently, this interval ranges from two to four days. The wait between image acquisition and surgery is a disadvantage inherent to the production of the customized STarFix™, but the primary disadvantages of the NEXFRAME™ are a consequence only of its mechanical design.

Therefore, a heretofore unaddressed need exists in the art to address the aforementioned deficiencies and inadequacies.

SUMMARY OF THE INVENTION

The present invention, in one aspect, relates to a surgical platform. In one embodiment, the surgical platform includes a ring structure having a first end portion, and an opposite, second end portion, and a body portion therebetween, where the body portion defines a housing extending between the first and second end portions. The surgical platform also includes a ball joint that is configured to be received in the housing of the ring structure and be rotatable around its center, where the ball joint defines at least one bore for accommodating a probe therethrough. The surgical platform further includes a plurality of leg assemblies. Each leg assembly comprises a first leg member having a joint portion detachably connected to the ring structure, an exteriorly threaded shank portion extending away from the joint portion, and an axis through the joint portion and the exteriorly threaded shank portion; a second leg member having a joint portion, an exteriorly threaded shank portion extending away from the joint portion, and an axis through the joint portion and the exteriorly threaded shank portion; and a sleeve member having a first end portion and an opposite, second end portion defining a sleeve body therebetween, and an axis through the sleeve body, where the sleeve body defines a chamber interiorly threaded for engaging with the first and second leg members, respectively.

As assembled, the threaded shank portions of the first and second leg members are received in the chamber through the first and second end portions of the sleeve member, respectively, such that the axes of the first and second leg members are substantially coincident with the axis of the sleeve member, and the first and second leg members are movable back and forth along the axis of the sleeve member when the sleeve member is being rotated around its axis, thereby adjusting a leg length defined between the joint portion of the first leg member and the joint portion of the second leg member. In one embodiment, the plurality of leg assemblies is equiangularly apart from each other.

In one embodiment, the joint portion of the first leg member of each leg assembly is connected to the ring structure through a one-dimension motion joint mechanism. In one embodiment, the ring structure has a plurality of tabs extending radially away from the body portion of the ring structure, each tab defining a hole therein; and the joint portion of the first leg member of each leg assembly comprises a forked structure having a pair of spaced parallel plates, each plate defining a hole therein. As assembled, the forked structure of the first leg member of each leg assembly is pivotally connected to a corresponding tab of the ring structure by a pivotal member passing through the holes of the pair of spaced parallel plates of the forked structure of the first leg member of the leg assembly and the corresponding tab of the ring structure such that the leg assembly is rotatable around the pivotal member. In another embodiment, the ring structure has a plurality of pairs of tabs extending radially away from the body portion of the ring structure, each tab defining a hole therein; and the joint portion of the first leg member of each leg assembly comprises a plate defining a hole therein. As assembled, the plate of the first leg member of each leg assembly is pivotally connected to a corresponding pair of tabs of the ring structure by a pivotal member passing through the holes of the corresponding pair of tabs of the ring structure and the plates of the first leg member of the leg assembly such that the leg assembly is rotatable around the pivotal member.

In another embodiment, the joint portion of the first leg member of each leg assembly is connected to the ring structure through a socket-ball joint mechanism. The ring structure has a plurality of sockets formed in the second end portion, where the joint portion of the first leg member of each leg assembly comprises a ball joint. As assembled, the ball joint of the first leg member of each leg assembly is received by a corresponding socket of the ring structure such that the leg assembly is rotatable around the center of the ball joint.

In yet another embodiment, the ring structure has a first plurality of tabs extending radially and outward from the body portion of the ring structure, each tab defining a hole therein, and a second plurality of sockets formed at the second end portion. The plurality of leg assemblies has a plurality of first leg assemblies and a plurality of second leg assemblies. The joint portion of the first leg member of each first leg assembly has a forked structure having a pair of spaced parallel plates, each plate defining a hole therein. The joint portion of the first leg member of each second leg assembly has a ball joint. As assembled, the forked structure of the first leg member of each first leg assembly is pivotally connected to a corresponding tab of the ring structure by a pivotal member passing through the holes of the pair of spaced parallel plates of the forked structure of the first leg member of the leg assembly and the corresponding tab of the ring structure, and the ball joint of the first leg member of each leg assembly is received by a corresponding socket of the ring structure, respectively.

In an alternative embodiment, the joint portion of the first leg member of each leg assembly is connected to the ring structure through a ring-type clamp with a threaded locking nut.

Additionally, the surgical platform also include a plurality of support members detachably mounted onto an anatomical structure, each support members having a ball portion. In one embodiment, each support member comprises a trackable fiducial marker. The joint portion of the second leg member of each leg assembly comprises a forked structure having a pair of spaced plates and a securing member adjustably mounted onto the pair of spaced plates, each plate defining a hole for accommodating the ball portion of a support member to form a socket-ball joint mechanism therein. As assembled, the pair of spaced plates of the forked structure of the second leg member of each leg assembly is connected to the ball portion of a corresponding support member through the socket-ball joint mechanism and secured thereto by adjusting the securing member such that the second leg member of the leg assembly is rotatable around the center of the ball portion of the corresponding support member.

Furthermore, the surgical platform may include a locking knob located at the body portion of the ring structure and adapted for adjustably locking the ball joint against movement relative to the ring structure.

The surgical platform is made from one or more metallic materials or from one or more plastic materials.

In another aspect, the present invention relates to a surgical platform. In one embodiment, the surgical platform includes a ring structure having a first end portion, an opposite, second end portion, and a body portion therebetween, where the body portion defines a housing extending between the first and second end portions; a ball joint configured to be received in the housing of the ring structure and be rotatable around the center of the ball joint, where the ball joint defines at least one bore for accommodating a probe therethrough; and a plurality of leg assemblies connected to the ring structure.

Each leg assembly has a first leg member and a second leg member, each of the first and second leg members having a joint portion and a shank portion extending from the joint portion, respectively; and a sleeve member having a first end portion and an opposite, second end portion defining a sleeve body therebetween, and an axis through sleeve body, where the sleeve body defines a chamber. In one embodiment, at least one of the shank portions of the first and second leg member is exteriorly threaded, and the chamber of the sleeve member has at least one interiorly threaded portion proximate to one of the first and second ends of the sleeve member for engaging with the at least one of the shank portions of the first and second leg member. As assembled, the shank portions of the first and second leg members are received by the chamber through the first and second end portions of the sleeve member, respectively, such that the first and second leg members and the sleeve member are coaxial, and at least one of the first and second leg members is movable back and forth along the axis of the sleeve member when the sleeve member is rotated around the axis, thereby adjusting a leg length defined between the joint portion of the first leg member and the joint portion of the second leg member.

In one embodiment, the joint portion of the first leg member of each leg assembly is connected to the ring structure through a motion joint mechanism. In another embodiment, the joint portion of the first leg member of each leg assembly is connected to the ring structure through a socket-ball joint mechanism. In an alternative embodiment, the joint portion of the first leg member of each leg assembly is connected to the ring structure through a ring-type clamp with a threaded locking nut. The plurality of leg assemblies is equiangularly apart from each other.

The surgical platform further includes a plurality of support members detachably mounted onto an anatomical structure, where each of the plurality of support members has a ball portion. The joint portion of the second leg member of each leg assembly comprises a forked structure having a pair of spaced parallel plates and a securing member adjustably mounted onto the pair of spaced parallel plates, each plate defining a hole for accommodating the ball portion of a support member to form a socket-ball joint mechanism therein. As assembled, the pair of spaced parallel plates of the forked structure of the second leg member of each leg assembly is connected to the ball portion of a corresponding support member through the socket-ball joint mechanism and secured thereto by adjusting the securing member such that the second leg member of the leg assembly is rotatable around the center of the ball portion of the corresponding support member.

Additionally, the surgical platform includes a locking knob located at the body portion of the ring structure and adapted for adjustably locking the ball joint against movement relative to the ring structure.

In yet another aspect, the present invention relates to a surgical platform. The surgical platform is made from one or more metallic materials or from one or more plastic materials. In one embodiment, the surgical platform includes a ring structure; a ball joint housed in the ring structure, where the ball joint defines at least one bore for accommodating a probe therethrough; and a plurality of leg assemblies.

Each leg assembly has a leg member having a joint portion connected to the ring structure and an exteriorly threaded shank portion extending away from the joint portion, and an axis through the joint portion and the exteriorly threaded shank portion; a foot member having a ball joint and a foot portion extending away from ball joint; and a sleeve member having a first end portion and an opposite, second end portion defining a sleeve body therebetween, and an axis through the sleeve body, where the sleeve body defines a chamber extending from the first end portion to the second end portion, and where the chamber is formed with an interiorly threaded portion proximate to the first end portion for engaging with the leg member, and a housing at the second end portion for accommodating the ball joint of the foot member. As assembled, the ball joint of the foot member is received in the housing of the chamber of the sleeve member, the joint portion of the leg member is connected to the ring structure, the threaded portion of the leg member is received by the threaded portion of the chamber of the sleeve member such that the axis of the leg member is substantially coincident with the sleeve axis and the leg member is movable back and forth along the sleeve axis when the sleeve member is being rotated around the sleeve axis, thereby adjusting a leg length defined between the joint portion of the leg member and the second end portion of the sleeve member.

In one embodiment, the joint portion of the first leg member of each leg assembly is connected to the ring structure through a motion joint mechanism. In another embodiment, the joint portion of the first leg member of each leg assembly is connected to the ring structure through a socket-ball joint mechanism. In an alternative embodiment, the joint portion of the first leg member of each leg assembly is connected to the ring structure through a ring-type clamp with a threaded locking nut. The plurality of leg assemblies is equiangularly apart from each other.

In one embodiment, the foot portion of the foot member has a first portion proximate to the ball joint and a second portion extending from the first portion, where the first portion and the second portion defines an angle, $\theta$, in a range of about 90-180 degree, where the angle $\theta$ defined between the first portion and the second portion of the foot member is substantially about 120 degree.

The surgical platform further includes a plurality of posts, each post mounted onto a base and adapted for supporting a corresponding foot member on the base, where each of the plurality of posts is configured to support a trackable fiducial marker.

In a further aspect, the present invention relates to a surgical platform. In one embodiment, the surgical platform includes a base portion configured to receive at least one probe; a plurality of adjustable legs configured to support the base portion, each adjustable legs having a first end portion and an opposite, second end potion defining a length therebetween; and at least one movable portion configured to adjust the length of at least one adjustable leg. The at least one movable portion in one embodiment comprises a sleeve member. The sleeve member has a first end portion and an opposite, second end portion defining a sleeve body therebetween, the sleeve body defining a chamber therein.

In one embodiment, each adjustable leg comprises a first leg member and a second leg member, each leg member having a joint portion and a shank portion extending from the joint portion, where the shank portions of the first and second leg members are received in the chamber of the sleeve member through the first and second end portion of the sleeve member, respectively, such that the joint portions of the first and second leg members are corresponding to the first and second end portion of the corresponding adjustable leg, respectively. In one embodiment, at least one of the shank portions of the first and second leg member is exteriorly threaded, and the chamber of the sleeve member has at least one interiorly threaded portion proximate to one of the first and second ends of the sleeve member for engaging with the at least one of the shank portions of the first and second leg member.

In one embodiment, the base portion comprises a ring structure. The first end portion of each adjustable leg is connected to the ring structure through a motion joint. In one embodiment, the first end portion of each of adjustable leg is connected to the ring structure through a socket-ball joint mechanism. In another embodiment, the first end portion of each adjustable leg is connected to the ring structure through a ring-type clamp with a threaded locking nut.

Furthermore, the surgical platform includes a plurality of foot members, each foot member comprising a joint means for connecting the foot member to a corresponding leg member by the second end portion of the leg member, where a joint means comprises a ball joint.

Moreover, the surgical platform includes means for detachably mounting the plurality of adjustable legs onto a plurality of support members detachably mounted onto an anatomical structure, where each support member comprises a trackable fiducial marker.

Additionally, the surgical platform includes means for accommodating a probe, where the accommodating means comprises a ball joint adapted for adjusting the trajectory of the probe.

In yet a further aspect, the present invention relates to a method of performing a surgical procedure with a surgical platform having a ring structure, a ball joint housed by the ring structure and a plurality of leg assemblies placed on a site of interest for supporting the ring structure, and a probe having a working end and accommodated by the ball joint. In one embodiment, the method comprises the steps of adjusting the ball joint to bring the working end of the probe to an initial optimal position at the site of interest; and adjusting the plurality of leg assemblies to bring the working end of the probe onto a final position from the initial optimal position, where the final position is corresponding to a surgical target of interest. In one embodiment, the step of adjusting the plurality of leg assemblies comprises the steps of individually adjusting a length of each leg assembly; and locking the corresponding leg assembly so as to remain the leg length unchanged during the surgical procedure.

The method further comprises the step of locking the ball joint against movement relative to the ring structure when the probe is brought onto the initial optimal position.

In one aspect, the present invention relates to a fiducial marker, which is usable with a surgical platform of the present invention. In one embodiment, the fiducial marker has a ball portion defining a recess; a shank portion extending from the ball portion; a threaded portion extending from the shank portion for threading into an anatomical structure; and a flange radially and outward extending from the junction of the shank portion and the threaded portion and having a first surface facing the shank portion and an opposite, second surface facing the threaded portion, where the second surface has a serration pattern formed such that when the fiducial marker is threaded solidly into an anatomical structure along a first direction, the serration pattern prevents the fiducial marker from moving along a second direction opposite to the first direction. The fiducial marker is made of a material that is imageable and/or trackable.

In one embodiment, the recess is adapted for accommodating a working end of a registration probe. The recess is in the form of a cone, a hemisphere, or a cylinder.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

Figure 1:
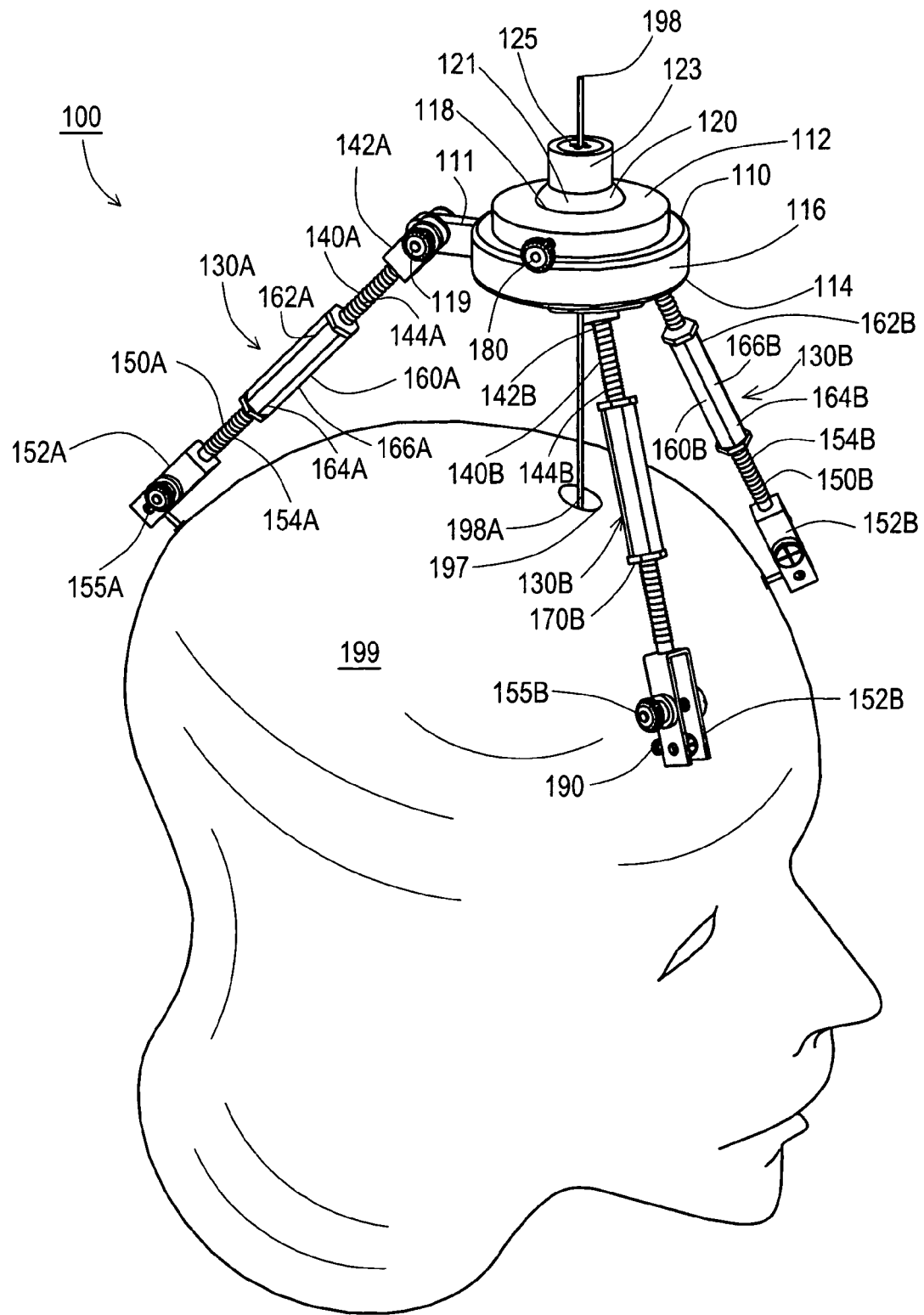
FIG. 1 shows a surgical platform according to one embodiment of the present invention.

The present invention is more particularly described in the following examples that are intended as illustrative only since numerous modifications and variations therein will be apparent to those skilled in the art. Various embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings in FIGS. 1-13. In accordance with the purposes of this invention, as embodied and broadly described herein, this invention, in one aspect, relates to a surgical platform usable for performing a surgical procedure.

The surgical platform, among other things, includes a ring structure, a ball joint housed in the ring structure, and a plurality of adjustable leg assemblies connected to the ring structure. The surgical platform also has an attachment of bone-implanted fiducials, which allows subsequent acquisition of a preoperative tomogram, and intraoperative optical tracking for aiming a probe at a target of interest. However, unlike the NEXFRAME™, the surgical platform provides ample space for burr-hole manipulation and ample surgical access. Furthermore, and more importantly, the surgical platform allows quick, easy, and precise targeting during a real time neuro-navigation. The surgical platform is attached to a surgical site of interest, for example, the skull of a patient, via a plurality of adjustable leg assemblies. Each leg assembly is attached to a base that supports a fiducial marker, or directly to a fiducial marker mounted onto the skull of the patient during a surgery procedure. The length of each leg assembly is independently adjustable. By adjusting each leg assembly independently, while watching a guiding icon of an image-guided surgical system on a display screen, a surgeon can fine-tune the trajectory of a probe with hand and without the need for a subsequent locking step. The guiding icon is related to the trajectory of the probe. In addition to the adjustable leg assemblies, the surgical platform includes an adjustable ball joint into which the probe is placed. In operation, the ball joint is first adjusted to bring the probe quickly to an initially optimal trajectory and locked. Then, by rotating the sleeve of each leg assembly, the surgeon, while watching the guiding icon, fine-tunes the orientation and position of the probe to the final optimal trajectory from the initially optimal trajectory of the probe.

In the surgical procedure performed with the surgical platform, an intraoperative guidance may be required, thus trackable fiducial markers are required during the surgical procedure. Because the surgical platform is attached to the same bases that support imageable fiducial markers during imaging, it may be necessary to provide a means for the base to support both a leg of the surgical platform and a trackable fiducial marker intraoperatively. Alternatively, it is practicable to provide a second set of bases so that each base supports either a leg of the surgical platform or a fiducial marker. Additionally, the surgical platform may be directly attached to a plurality of imageable fiducial markers during preoperative imaging and intraoperative tracking.

Referring now to FIG. 1, a surgical platform 100 is shown according to one embodiment of the present invention. The surgical platform 100 includes a ring structure 110. the ring structure 110 has a first end portion 112, an opposite, second end portion 114, and a body portion 116 therebetween, where the body portion 116 defines a housing 118 extending between the first and second end portions 112 and 114. The surgical platform 100 also includes a ball joint 120. The ball joint 120 has a ball portion 121 and a joint body (probe holder) 123 engaged with the ball portion 121. The ball portion 121 of the ball joint 120 is housed by the housing 118 of the ring structure 110 such that the ball joint 120 is rotatable around the center of the ball portion 121 relative to the ring structure 110. The joint body 123 of the ball joint 120 defines at least one bore 125 for accommodating a probe 198 therethrough. The surgical platform 100 may also include a locking knob 180 located at the body portion 116 of the ring structure 110 and adapted for adjustably locking the ball joint 120 against movement relative to the ring structure 110.

The surgical platform 100 further has three leg assemblies including a leg assembly 130A and two leg assemblies 130B. Other number of the leg assemblies can also be utilized to practice the present invention. Each leg assembly 130A (130B) comprises a first leg member 140A (140B), a second leg member 150A (150B) and a sleeve member 160A (160B). The first leg member 140A (140B) has a joint portion 142A (142B) connected to the ring structure 110 and an exteriorly threaded shank portion 144A (144B) extending from the joint portion 142A (142B) and an axis (not shown) through the joint portion 142A (142B) and the exteriorly threaded shank portion 144A (144B). The second leg member 150A (150B) has a joint portion 152A (152B) and an exteriorly threaded shank portion 154A (154B) extending from the joint portion 152A (152B) and an axis (not shown) through the joint portion 152A (152B) and the exteriorly threaded shank portion 154A (154B). The sleeve member 160A (160B) has a first end portion 162A (162B) and an opposite, second end portion 164A (164B) defining a sleeve body 166A (166B) therebetween, and an axis (not shown) through the sleeve body 166A (166B), where the sleeve body 166A (166B) defines a chamber (not shown) interiorly threaded for engaging with the first and second leg members 140A (140B) and 150A (150B). As shown in FIG. 1, as assembled, the threaded shank portions 144A (144B) and 154A (154B) of the first and second leg members 140A (140B) and 150A (150B) are received in the chamber through the first and second end portions 162A (162B) and 164A (164B) of the sleeve member 160A (160B), respectively. The axes of the first and second leg members 140A (140B) and 150A (150B) are substantially coincident with the axis of the sleeve member 160A (160B), i.e., the first leg members 140A (140B), the second leg members 150A (150B) and the sleeve member 160A (160B) are coaxial, as assembled. Furthermore, the first and second leg members 140 and 150 are movable back and forth along the axis of the sleeve member 160A (160B) when the sleeve member 160A (160B) is turned or rotated around the axis, thereby adjusting a leg length defined between the joint portion 142A (142B) of the first leg member 140A (140B) and the joint portion 152A (152B) of the second leg member 150A (150B).

As shown in FIG. 1, the joint portion 142A of the first leg member 140A of the leg assembly 130A is connected to the ring structure 110 through a one-dimension motion joint mechanism. The joint portion 142B of the first leg member 140B of each leg assembly 130B is connected to the ring structure 110 through a socket-ball joint mechanism. Other connection mechanism can also be used to practice the present invention. For example, the joint portion of the first leg member of each leg assembly can be connected to the ring structure through a ring-type clamp with a threaded locking nut. In the embodiment shown in FIG. 1, the joint portion 152A (152B) of the second leg member 150A (150B) of the leg assembly 130A (130B) is engaged with a corresponding support member 190 through a socket-ball joint mechanism and secured thereto by a securing member 155A (155B). Accordingly, the leg assembly 130A (130B) is rotatable around the corresponding support member 190. The support member 190 is mountable, and, as shown in FIG. 1, indeed mounted onto the skull 199 of a patient when it is in use. Additionally, the support member 190 is also used for target registration and localization, and thus preoperatively imageable and/or intraoperatively trackable. Preferably, the support member 190 includes a fiducial marker having a ball portion. In one embodiment, such a fiducial marker that is usable in connection with a surgical platform of the present invention is shown in FIG. 13 and described below in details.

In practice, a practitioner such as a surgeon firstly adjusts the ball joint 120 to bring the working end 198A of the probe 198 onto an initial optimal position in the surgical site 197 of interest, and then adjusts the locking knob 180 to lock the ball joint 120 against movement relative to the ring structure 110. Next, the surgeon performs fine tuning to bring the working end 198A of the probe 198a from the initial optimal position to a final optimal position. The fine tuning is performed by individually adjusting the length of each of the leg assemblies 130A and 130B, for example, individually rotating the sleeve member 160A (160B) of each of the leg assemblies 130A and 130B with hand. After the fine tuning, the leg assembly 130A (130B) may be locked by a locking nut 170A (170B) so as to remain the leg length of the leg assembly 130A (130B) unchanged during the surgical procedure. The initial optimal position and the final optimal position are corresponding to an entry point and a target point of surgery, respectively. According to the present invention, only the target point is fine tuned. The entry point is not as critical as the target point. During the fine tuning, as the orientation of the ring structure 110 (thus the surgical platform) is changed with adjusting the lengths of the leg assemblies 130A and 130B to bring the working end 198A of the probe 198 exactly onto the target point, the working end 198A of the probe 198 moves away from the initially chosen entry point (position). Among other things, one of the advantages of the surgical platform 100 of the present invention is that the fine tuning is performed only on the target position of surgery, while keeping the entry position within a millimeter or so of the roughly chosen entry point.

The surgical platform can be made of one or more metallic materials including titanium, alloy or the likes for multiple usages. The surgical platform can also be made of one ore more disposable plastics for single use.

The ring structure, the ball joint, the leg assemblies and their connection mechanisms utilized in the surgical platform of the present invention are further described in conjunction with FIGS. 2-9.

Figure 2A:
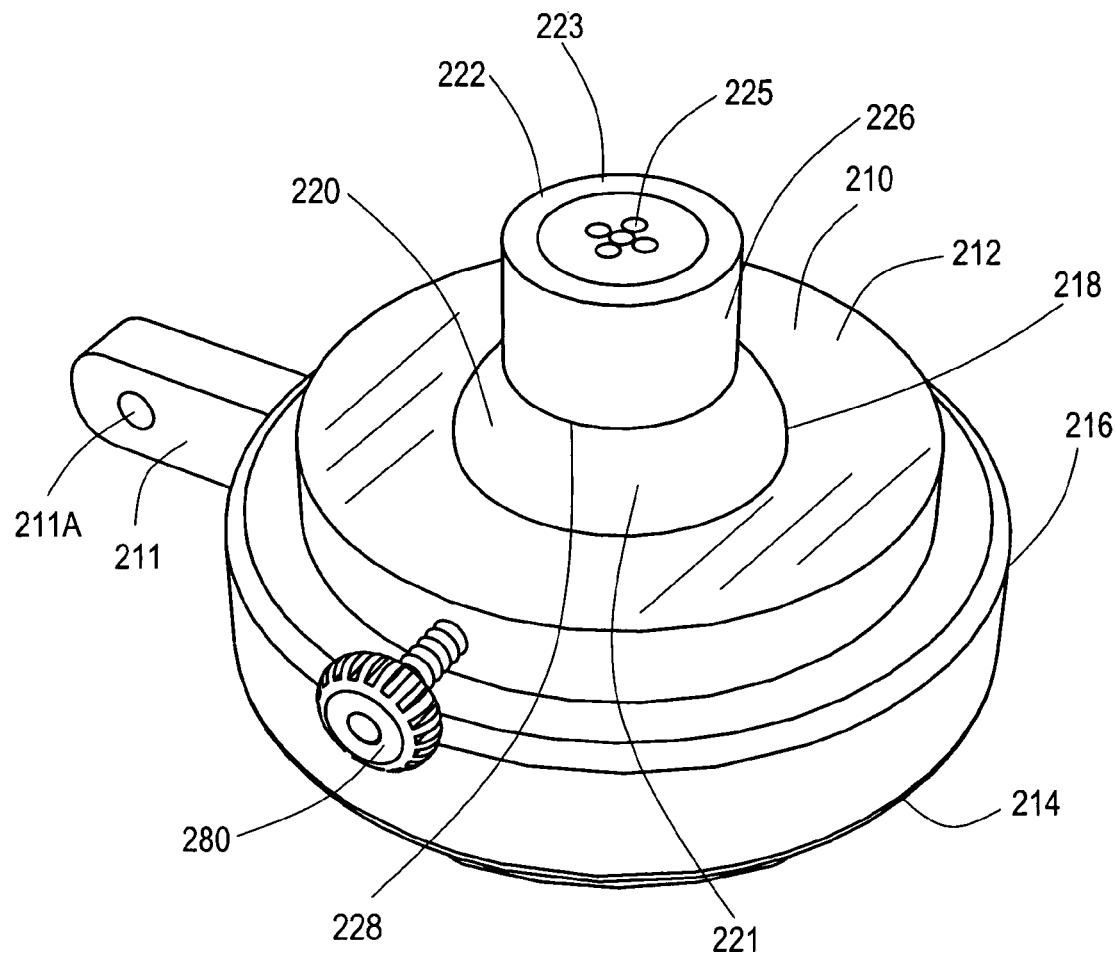
FIGS. 2A and 2B respectively show a top perspective view and a bottom perspective view of a ring structure and a ball joint housed in the ring structure according to one embodiment of the present invention.
Figure 2B:
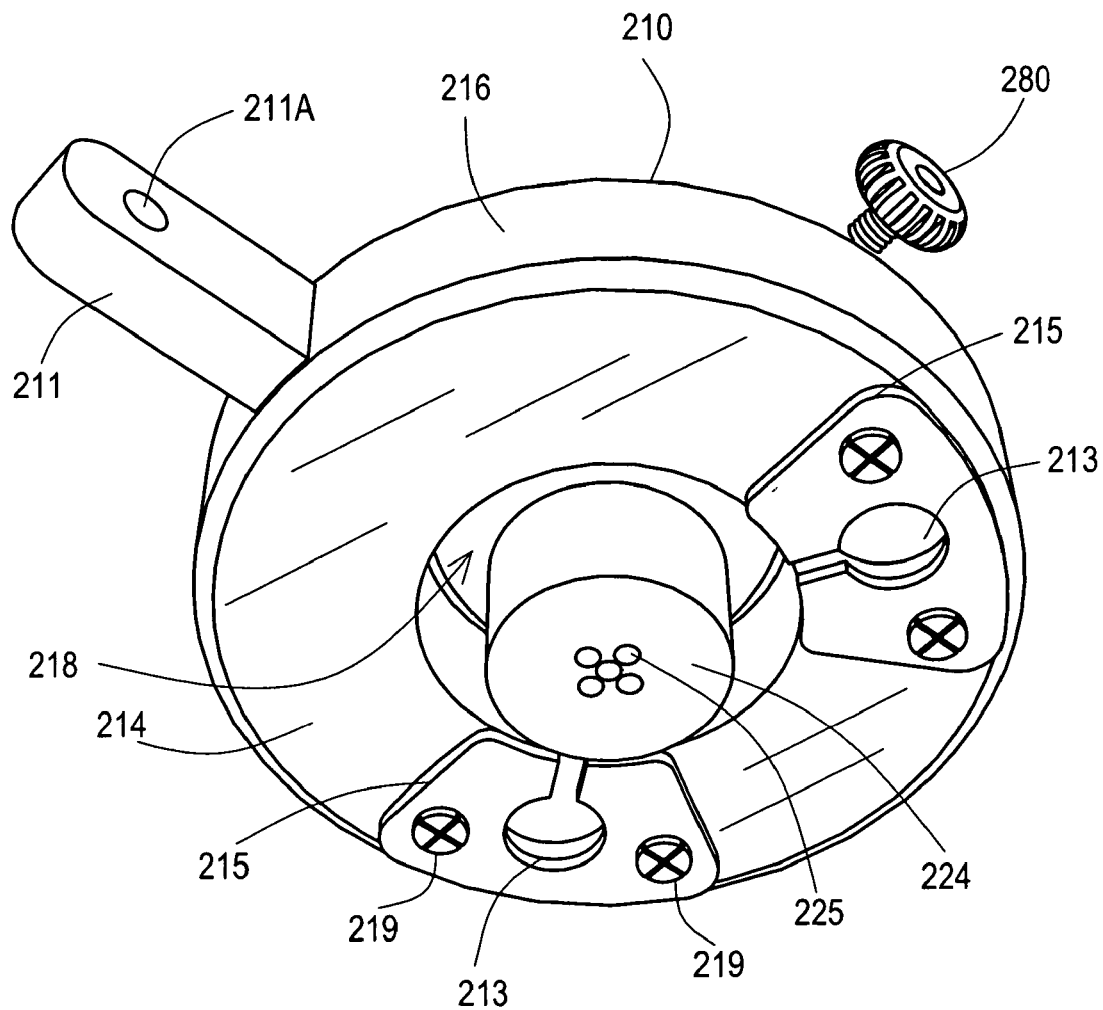

Referring to FIGS. 2A and 2B, a ring structure 210 and a ball joint 220 housed in the ring structure 210 are shown according to one embodiment of the present invention. The ring structure 110 has a first end portion 212 and an opposite, second end portion 214 defining a body portion 216 therebetween, and a housing 218 defined in the body portion 216 and extending between the first and second end portions 212 and 214. The ring structure 210 has a tab 211 extending radially and outward from the body portion 216. The tab 211 defines a pivot hole 211A therein. The ring structure 210 also has two sockets 213 formed on the second end portion 214. Each of the tab 211 and the sockets 213 is adapted for connecting a corresponding leg assembly to the ring structure 210. The connected leg assembly is secured thereto by either a screw or pin through the pivot hole 211A of the tab 211 of the ring structure 210 or a socket cover 215 detachably mountable to the second end portion 214 of the ring structure 210 by means of screws 219 or other securing means such as glue. For example, as shown in FIG. 1, the tab 111 is used to connect the ring structure 110 to the leg assembly 130A, while the socket is used to connect the ring structure 110 to the leg assembly 130B.

The connection of a leg assembly to the ring structure 210 through the tab 211 allows the leg assembly to rotate one-dimensionally around the pivot hole 211A. The connection of a leg assembly to the ring structure 210 through the socket 213 allows the leg assembly to rotate three-dimensionally around the socket 213. The former is through a one-dimension motion joint mechanism, while the latter is through a socket-ball joint mechanism.

The ball joint 220 has a ball portion 221 defining a chamber 228 extending from one side to the other side through the center of the ball portion 221, and a probe holder 223 received in the chamber 228 and having a first end portion 222 and an opposite, second end portion 224 defining a body portion 226 therebetween. The body portion 226 is formed to have at least one bore 225 that extends from the first end portion 222 to the second end portion 224 of the probe holder 223. The at least one bore 225 is adapted for accommodating a probe. The ball portion 221 of the ball joint 220 is housed in the housing 218 of the ring structure 210 such that the ball joint 220 is rotatable around the center of the ball joint 220 relative to the ring structure 210. As described above, the ball joint 220 is adapted for initially selecting an entry point of surgery for the probe. After the entry point of surgery is selected, the ball joint 220 is locked by a locking knob 280 located at the body portion 216 of the ring structure 210, which prevents the ball joint 220 from moving relative to the ring structure 210 during a surgical procedure.

Figure 3A:
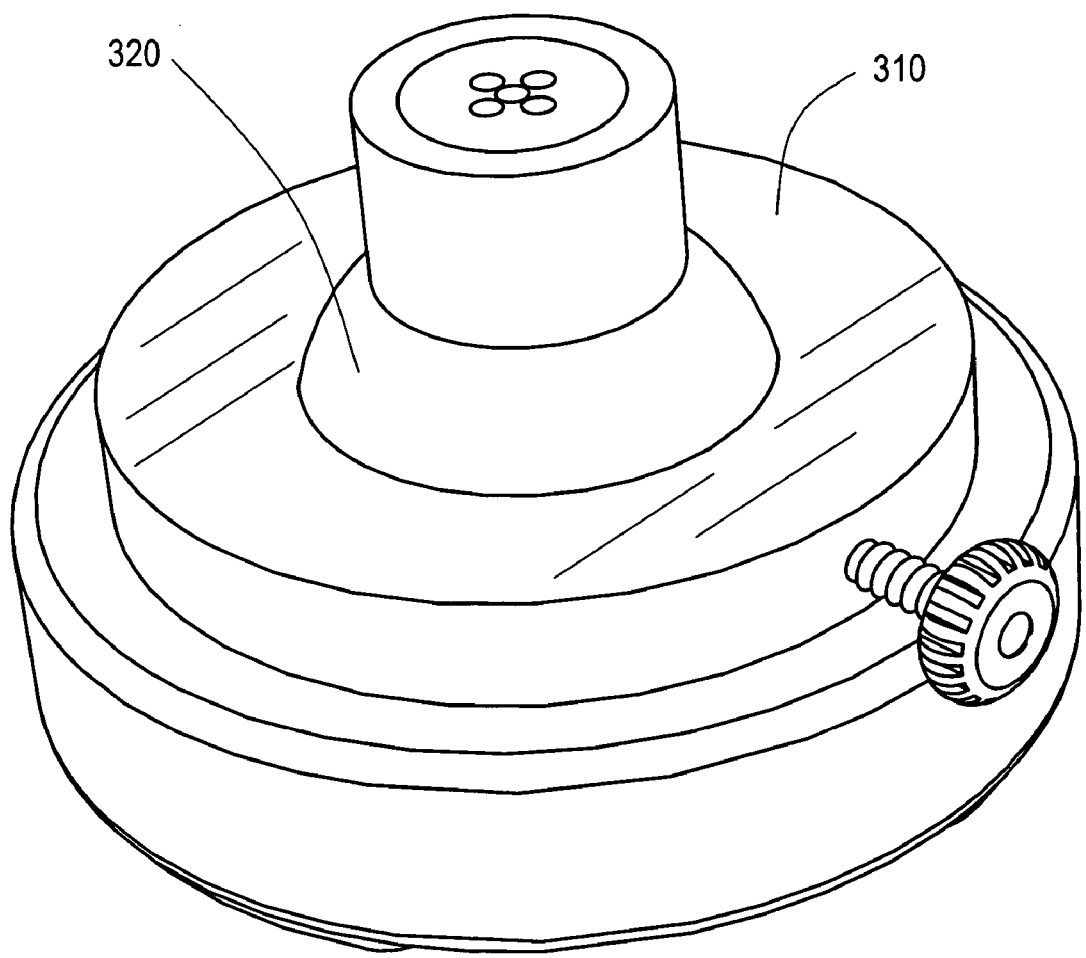
FIGS. 3A and 3B respectively show a top perspective view and a bottom perspective view of a ring structure and a ball joint housed in the ring structure according to another embodiment of the present invention.
Figure 3B:
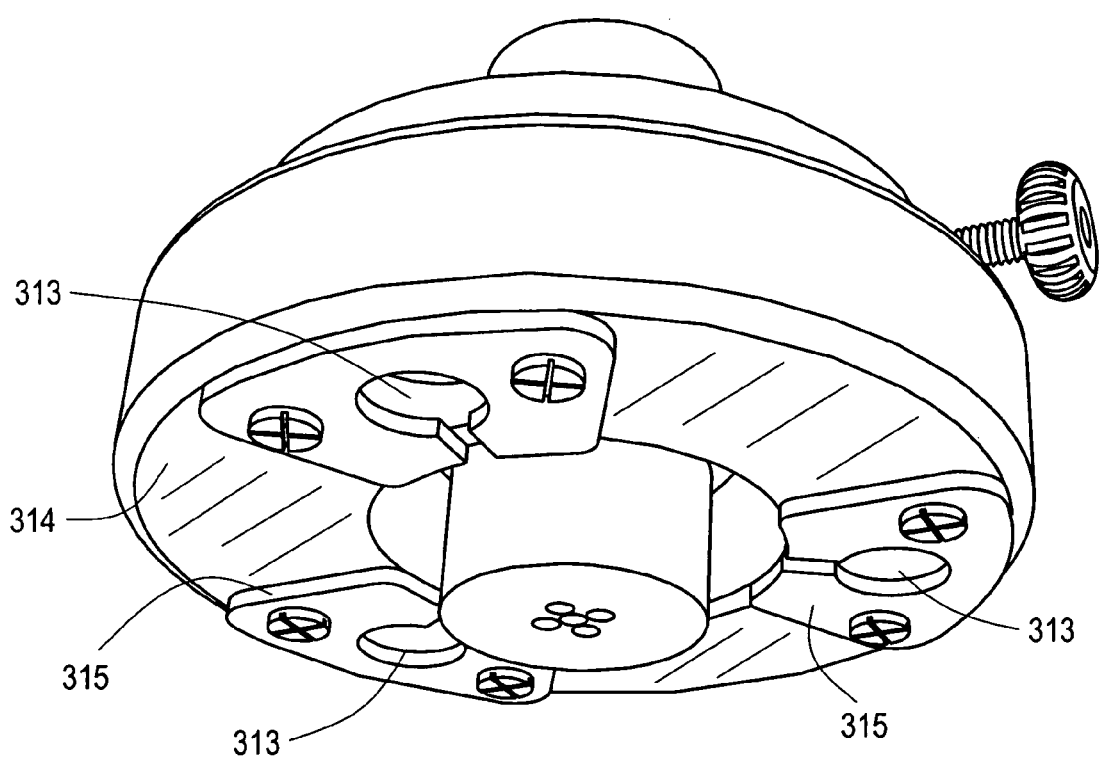

FIGS. 3A and 3B show a ring structure 310 and a ball joint 320 housed in the ring structure 310 according to another embodiment of the present invention. In this exemplary embodiment, the ball joint 320 is structurally same as the one shown in FIGS. 2A and 2B. However, the ring structure 310 has three sockets 313 formed on the second end portion 314 of the ring structure 310 and being equiangularly apart from each other. Accordingly, all three leg assemblies, as assembled, are connected to the ring structure 310 through a socket-ball joint mechanism, respectively. Each leg assembly is secured to the ring structure 310 by a socket cover 315 detachably mounted to the second end portion 314 of the ring structure 310 by means of screws 319. The socket cover 315 may be mounted to the second end portion 314 of the ring structure 310 by other securing means such as glue. In the example, each leg assembly is capable of rotating one-dimensionally around the pivot hole 311A of the tabs 311.

Figure 4:
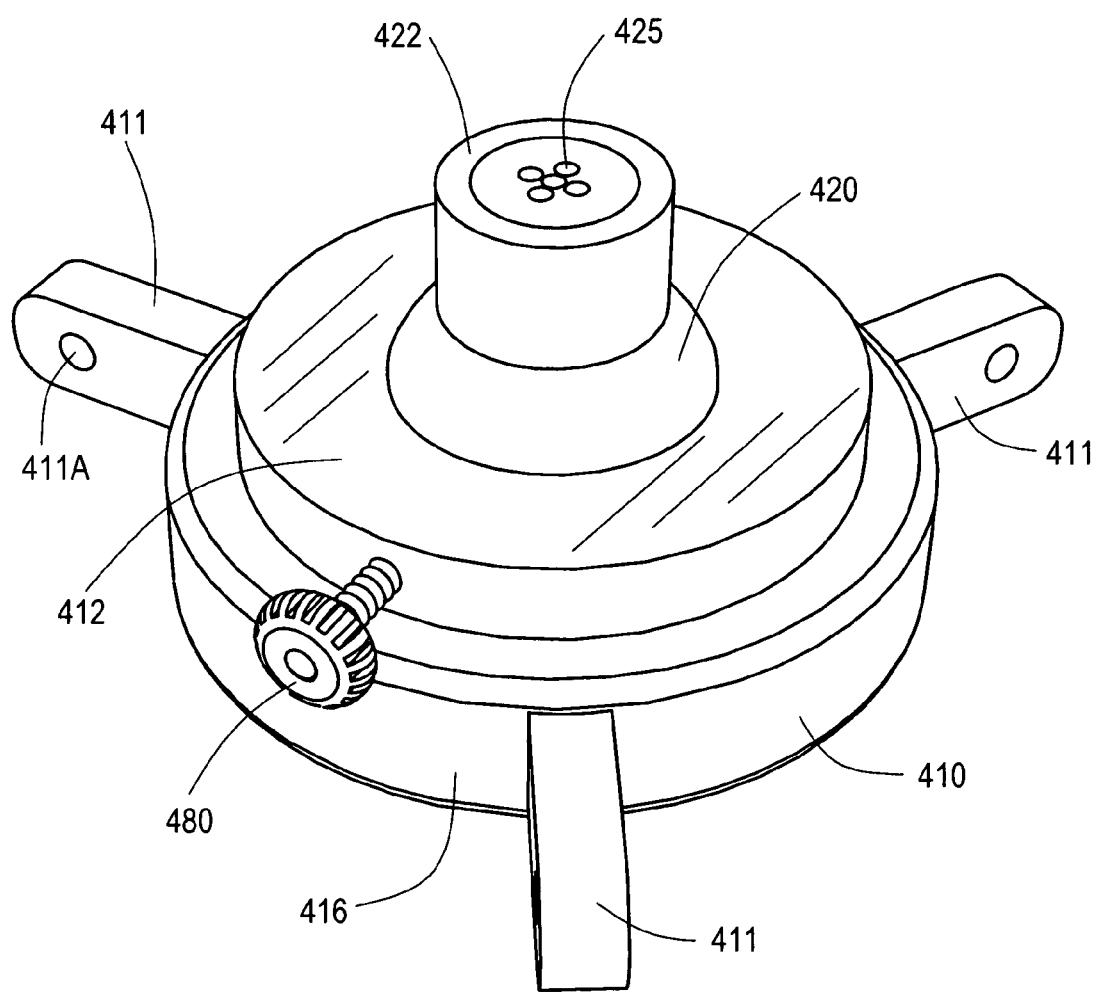
FIG. 4 shows a top perspective view of a ring structure and a ball joint housed in the ring structure according to an alternative embodiment of the present invention.

FIG. 4 shows an alternative embodiment of a ring structure 410 and a ball joint 420 housed in the ring structure 410 according to the present invention. The ball joint 420 is structurally same as the one shown in FIGS. 2A and 2B. However, the ring structure 410 has three tabs 411 extending radially away from the body portion 416 and being equiangularly apart from each other. In an alternative embodiment, the three tabs 411 may be formed non-equiangularly apart from each other. Each of the tabs 411 has a pivot hole 411A defined therein. In this embodiment, all three leg assemblies, as assembled, are connected to the ring structure 410 through a one-dimension motion joint mechanism. Each leg assembly is secured to the ring structure 410 by a screw or pin through the pivot hole 411A of the corresponding tab 411 of the ring structure 410.

Figure 5A:
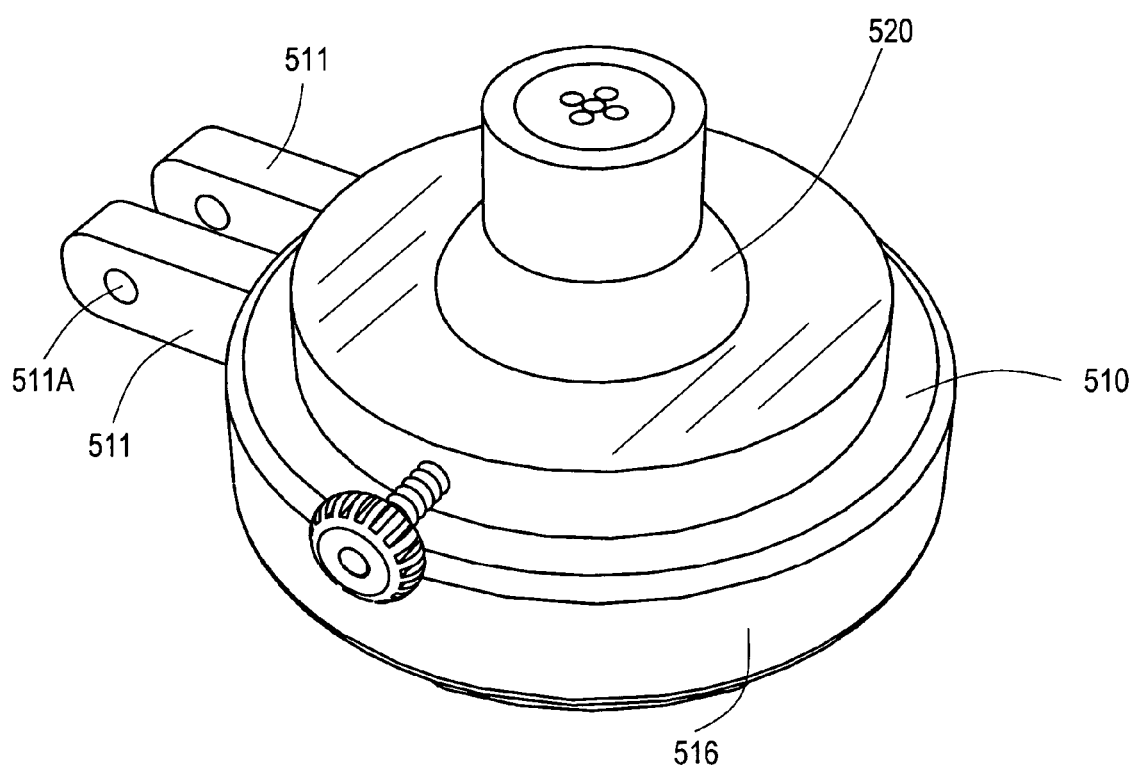
FIGS. 5A and 5B respectively show a top perspective view and a bottom perspective view of a ring structure and a ball joint housed in the ring structure according to one embodiment of the present invention.
Figure 5B:
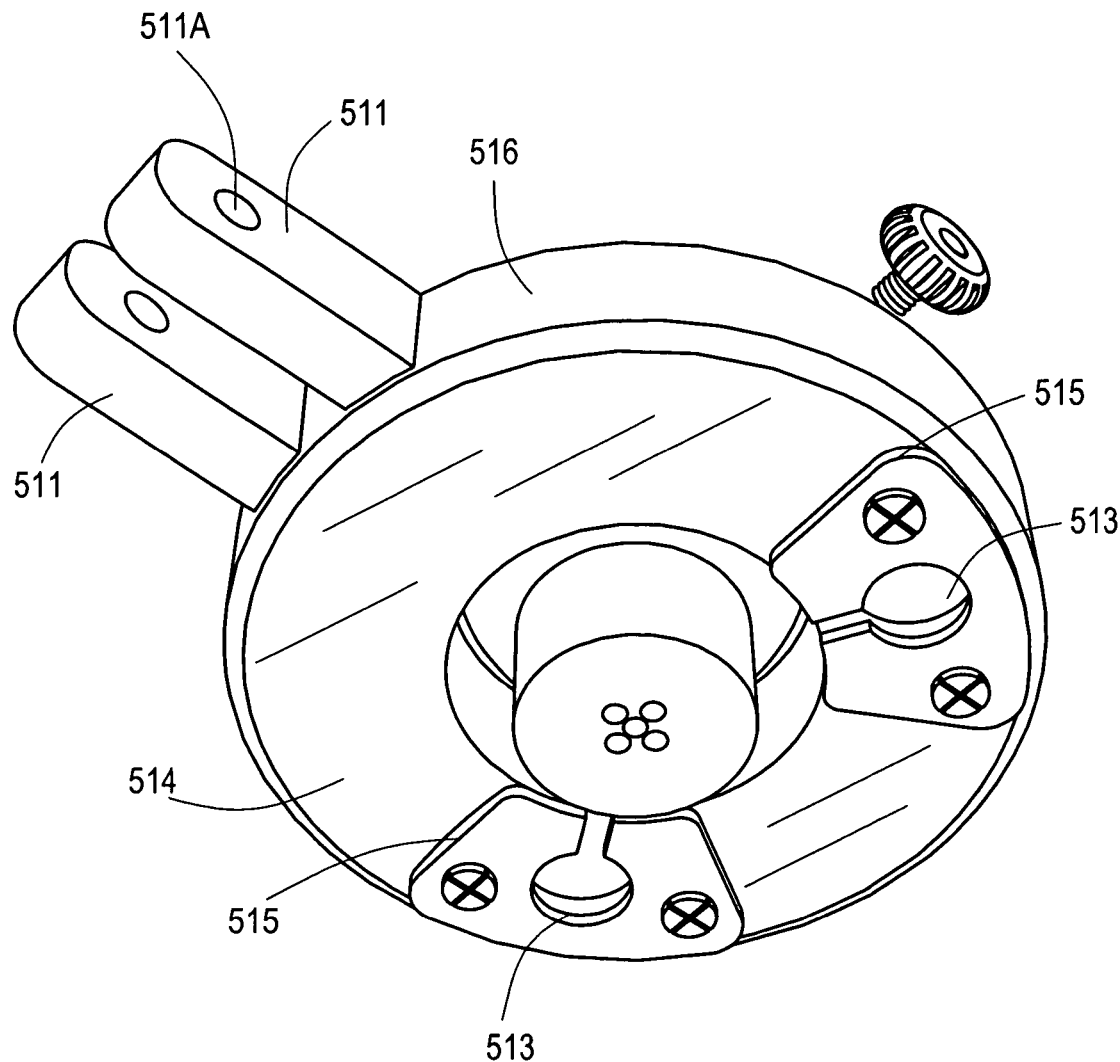

FIGS. 5A and 5B show a ring structure 510 and a ball joint 520 housed in the ring structure 510 according to one embodiment of the present invention. In this exemplary embodiment, the ball joint 520 is structurally same as the one shown in FIGS. 2A and 2B. However, the ring structure 510 has one pair of tabs 511 extending radially away from the body portion 516 of the ring structure 510, and two sockets 513 formed on the second end portion 514 of the ring structure 510. The pair of tabs 511 and the sockets 513 are spaced apart from each other. Additionally, each of the pair of tabs 511 has a pivot hole 511A formed therein, which is used to secure a leg assembly to the ring structure 510. The ring structure 510 also has two socket cover 515 detachably mountable to the second end portion 514 of the ring structure 510. Each socket cover 515 is used to secure a corresponding leg assembly to the ring structure 510. In this embodiment, the leg assembly connected to the ring structure 510 through the pair of tabs 511 is rotatable one-dimensionally around the pivot hole 511A of the pair of tabs 511, while the leg assembly connected to the ring structure 510 through the socket 513 is rotatable three-dimensionally around the socket 513.

Referring now to FIGS. 6-9, a leg assembly according to different embodiments of the present invention is shown.

Figure 6A:
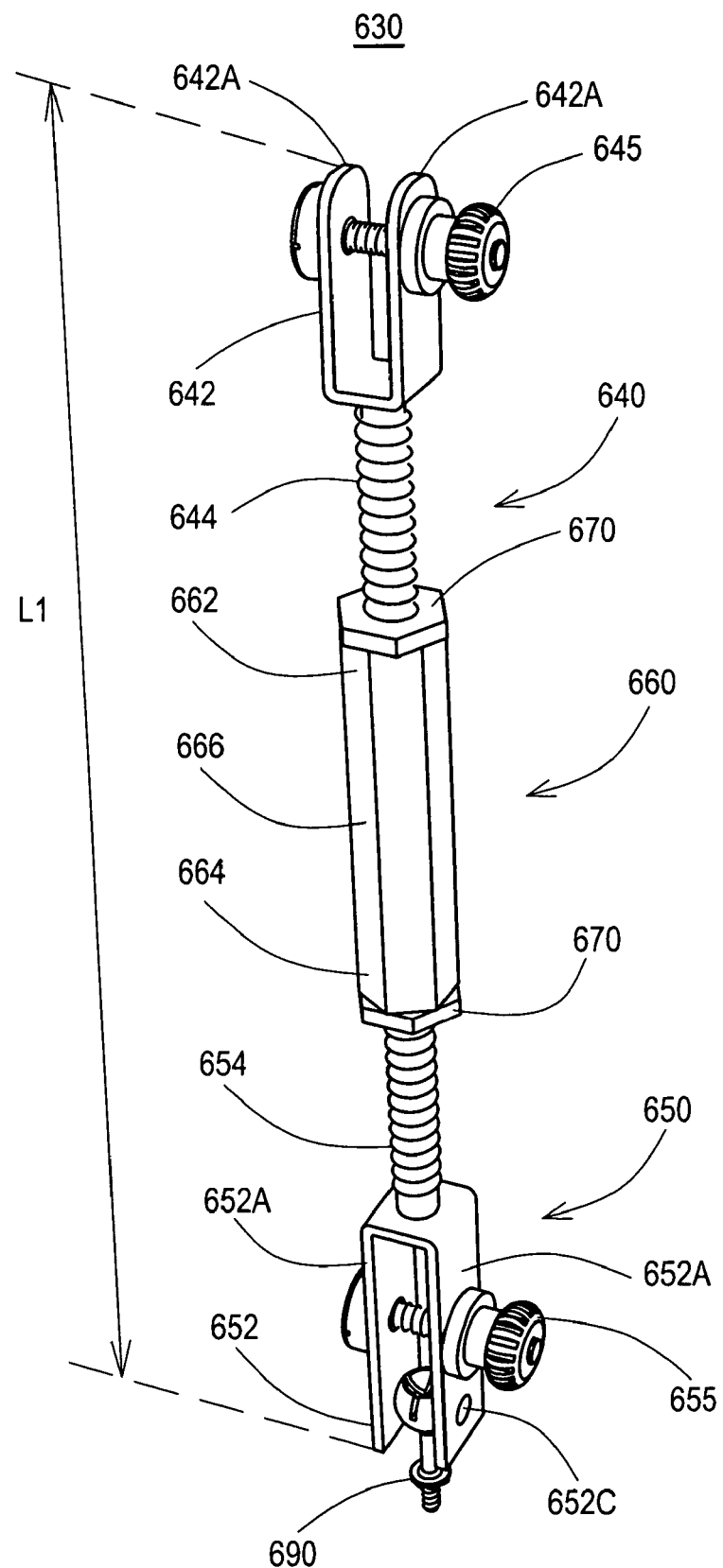
FIGS. 6A and 6B respectively show a perspective view and an exploded view of a leg assembly according to one embodiment of the present invention.
Figure 6B:
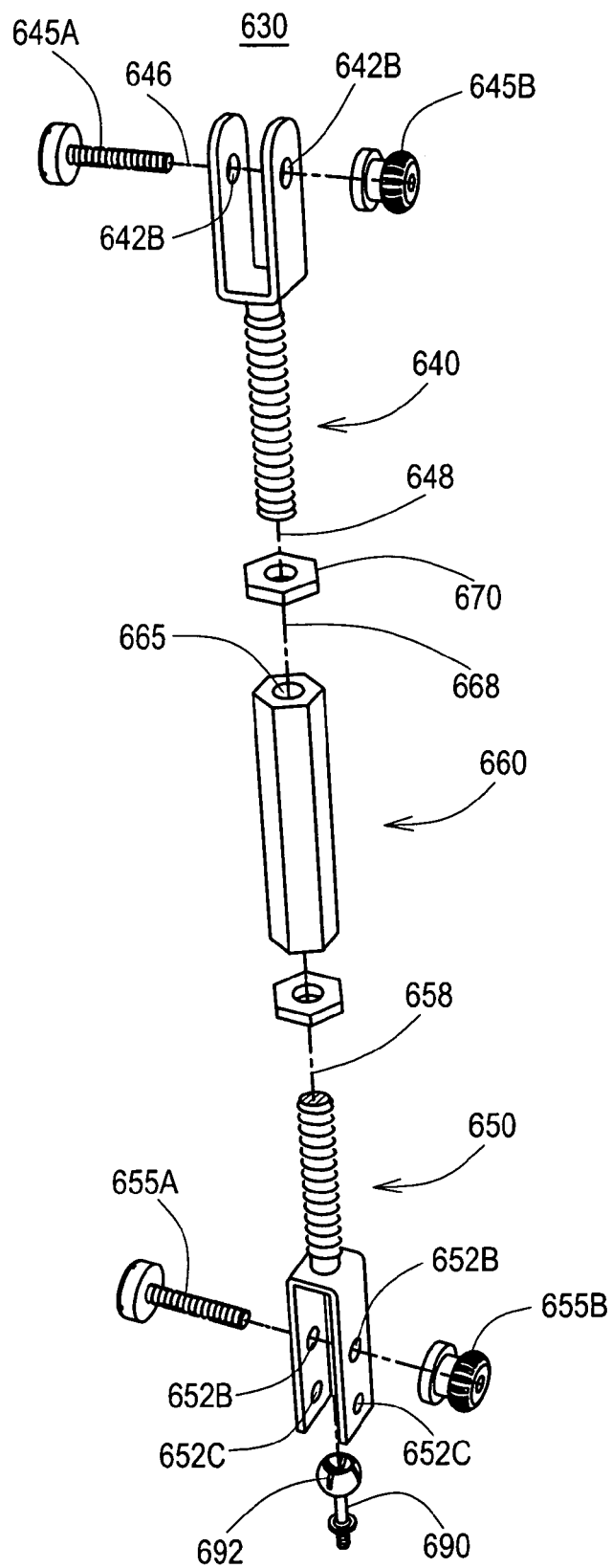

As shown in FIGS. 6A and 6B, a leg assembly 630 according to one embodiment of the present invention includes a first leg member 640, a second leg member 650 and a sleeve member 660. The first leg member 640 has a joint portion 642 and an exteriorly threaded shank portion 644 extending from the joint portion 642 and an axis 648 through the joint portion 642 and the exteriorly threaded shank portion 644. The joint portion 642 of the first leg member 640 has a forked structure having a pair of spaced parallel plates 642A, where each plate 642A defines a hole 642B therein. The second leg member 650 has a joint portion 652 and an exteriorly threaded shank portion 654 extending from the joint portion 652 and an axis 658 through the joint portion 652 and the exteriorly threaded shank portion 654. The joint portion 652 of the second leg member 650 includes a forked structure having a pair of spaced parallel plates 652A. Each plate 652A has a first hole 652B and a second hole 652C formed therein. The sleeve member 660 has a first end portion 662 and an opposite, second end portion 664 defining a sleeve body 666 therebetween, and an axis 668 through the sleeve body 666. The sleeve body 666 defines a chamber 665 that is interiorly threaded for engaging with the first and second leg members 640 and 650. In this embodiment, the sleeve member 660 is formed as a polygonal column. Other types of the sleeve members, such as a cylinder, can also be utilized to practice the present invention.

As assembled, the threaded shank portions 644 and 654 of the first and second leg members 640 and 650 are received in the chamber 665 through the first and second end portions 662 and 664 of the sleeve member 660, respectively, as shown in FIG. 6A. Furthermore, the axes 648 and 658 of the first and second leg members 640 and 650 are substantially coincident with the axis 668 of the sleeve member 660. The leg assembly 630 has a leg length, L1, defined between the joint portion 642 of the first leg member 640 and the joint portion 652 of the second leg member 650. According to the present invention, the first and second leg members 640 and 650 and the sleeve member 660 are adapted such that the first and second leg members 640 and 650 are moving back and forth along the axis 668 of the sleeve member 660 as the sleeve member 660 is being rotated around the axis 668, thereby adjusting the leg length L1 of the leg assembly 630. The leg length L1 of the leg assembly 630 can be fixed at a desired length by adjusting locking nuts 670.

The leg assembly 630 is connectable to a ring structure through a one-dimension motion joint mechanism. That is, the forked structure of the first leg member 640 of the leg assembly 630 is pivotally connected to a corresponding tab of the ring structure by a pivotal member 645 that passes through the holes 642B of the pair of spaced parallel plates 642A of the forked structure of the first leg member 640 and the hole of the corresponding tab of the ring structure. Accordingly, the leg assembly 630 is rotatable one-dimensionally around the pivotal member 645 (or an axis 646 passing through the holes 642B of the pair of spaced parallel plates 642A of the forked structure and the corresponding tab). In this exemplary example, the pivotal member 645 includes a screw 645A and a screw nut 645B detachably mountable to the screw 645A. Other types of the pivotal members, such as a pin, can also be utilized to practice the present invention.

Additionally, the leg assembly 630 is connectable to a support member 690 through a socket-ball joint mechanism. The support member 690, as disclosed below, has a ball portion 692 and is mountable to the skull of a patient. Specifically, the pair of spaced parallel plates 652A of the forked structure of the second leg member 650 of the leg assembly 630 is configured to clamp the ball portion 692 of the support member 690 such that the holes 652C of the pair of spaced parallel plates 652A are in communication with the ball portion 692 of the support member 690 through a socket-ball joint mechanism. The second leg member 650 of the leg assembly 630 is rotatable around the center of the ball portion 692 of the support member 690. The connection of the leg assembly 630 to the support member 690 is further secured by the securing member 655 having a screw 655A and a screw nut 655B detachably mountable to the screw 655A.

Figure 7:
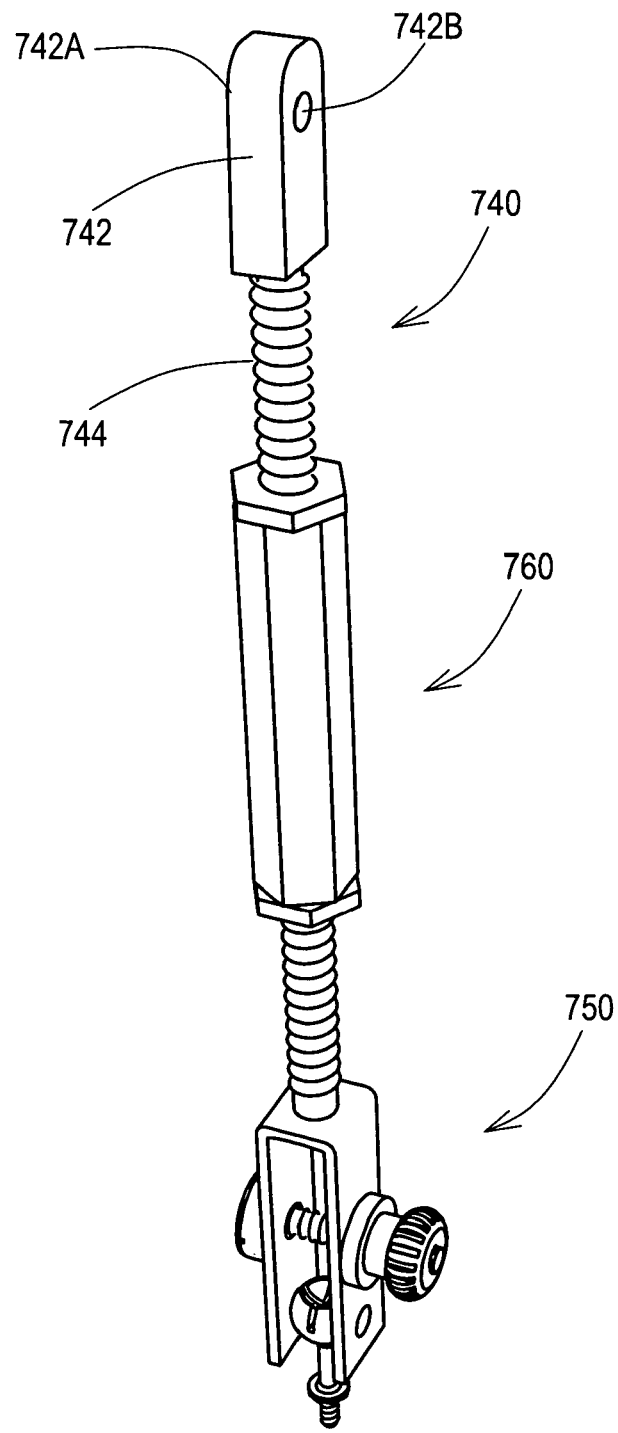
FIG. 7 shows a perspective view of a leg assembly according to another embodiment of the present invention.

FIG. 7 shows another embodiment of a leg assembly 730 of the present invention. The leg assembly 730, similar to the one shown in FIGS. 6A and 6B, has a first leg member 740, a second leg member 750 and a sleeve member 760. The second leg member 750 and the sleeve member 760 are same as those shown in FIGS. 6A and 6B. However, the first leg member 740 has a joint portion 742 that includes a single plate 742A, and a threaded shank portion 744 extending from the single plate 742A. In the exemplary embodiment, the leg assembly 730 is connected to a ring structure through a pair of tabs shown in FIGS. 5A and 5B. That is, the plate 742A of the first leg member 740 of the leg assembly 730 is placed between the pair of tabs of the ring structure and secured by a pivotal member, such as a screw or pin, passing through the holes of the pair of tabs of the ring structure and hole 742B of the plate 742A of the first leg member 740 of the leg assembly 730. Accordingly, the leg assembly 730 is rotatable one-dimensionally around the pivotal member.

Figure 8A:
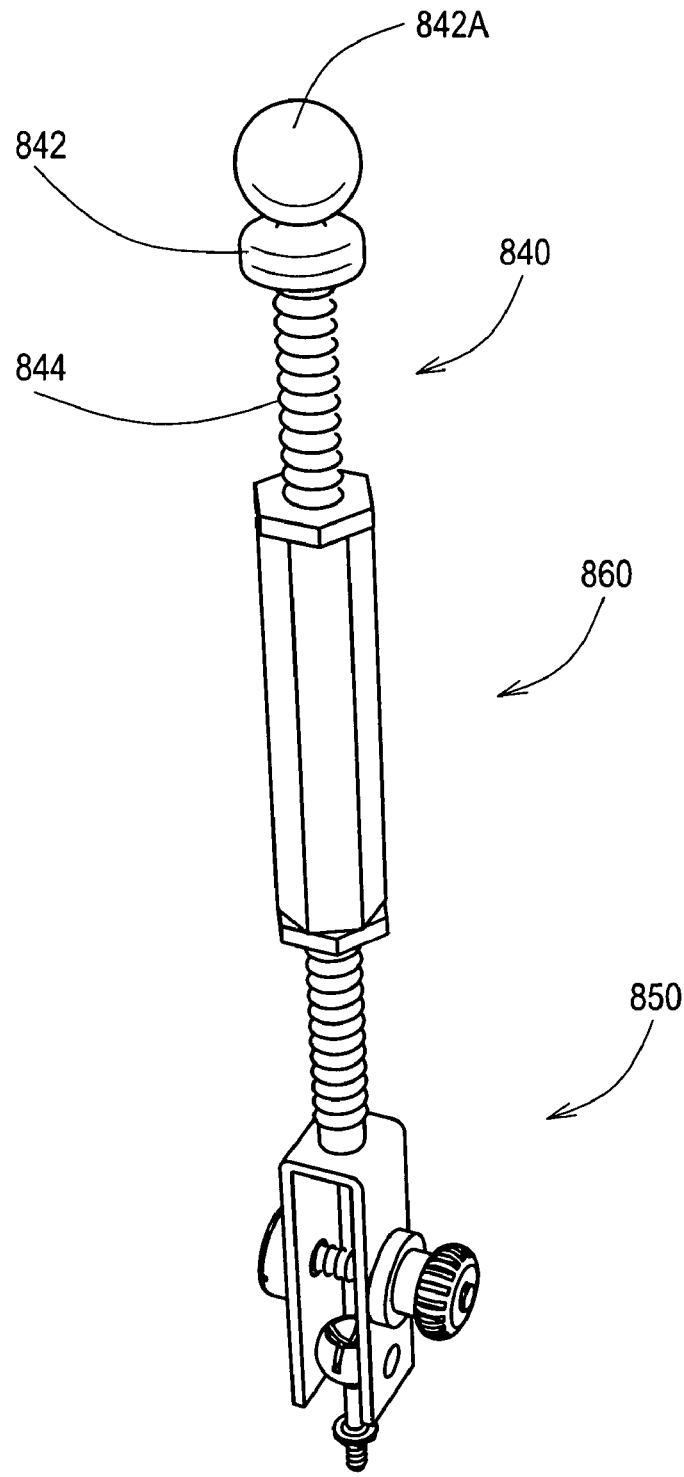
FIGS. 8A and 8B respectively show a perspective view and an exploded view of a leg assembly according to an alternative embodiment of the present invention.
Figure 8B:
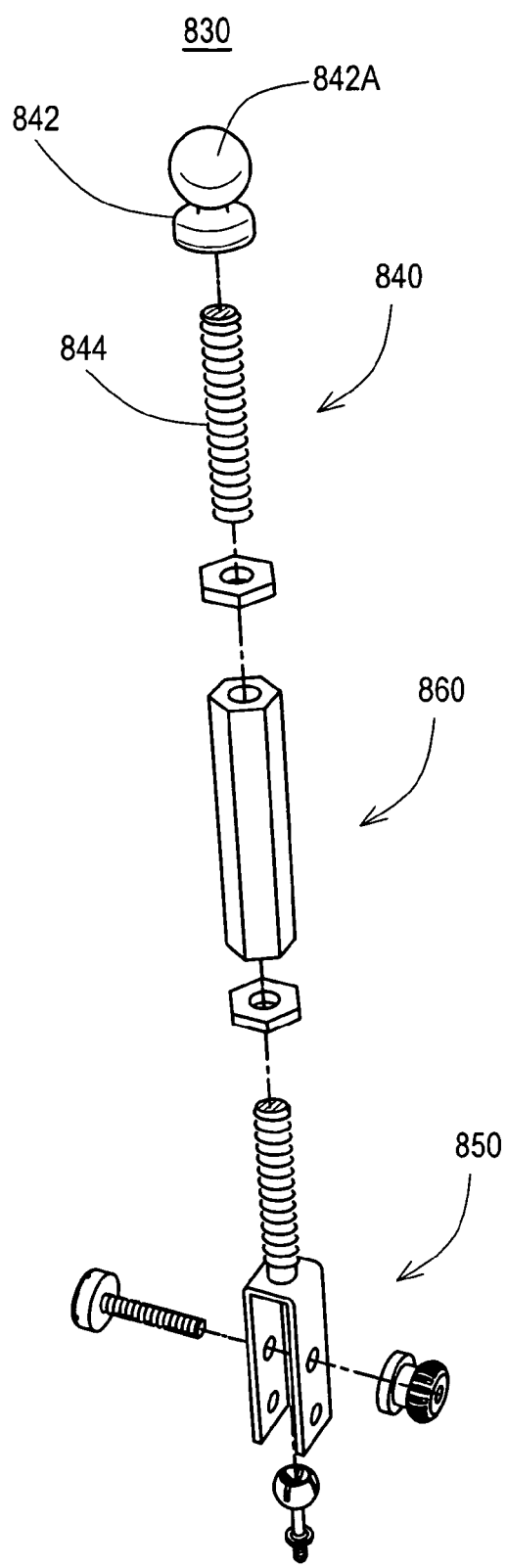

FIGS. 8A and 8B show a leg assembly 830 according to an alternative embodiment of the present invention. The leg assembly 830, similar to the one shown in FIGS. 6A and 6B, has a first leg member 840, a second leg member 850 and a sleeve member 860. The second leg member 850 and the sleeve member 860 are structurally same as those shown in FIGS. 6A and 6B. However, the first leg member 840 has a joint portion 842 that includes a ball joint 842A and a threaded shank portion 844 attached to the ball joint 842A. As assembled, the ball joint 842A of the first leg member 840 of the leg assembly 830 is received by a corresponding socket of a ring structure shown in FIGS. 2, 3 and 5. Accordingly, the leg assembly 830 is connected to a ring structure through a socket-ball joint mechanism. The leg assembly 830 is rotatable around the corresponding socket of the ring structure.

Figure 9A:
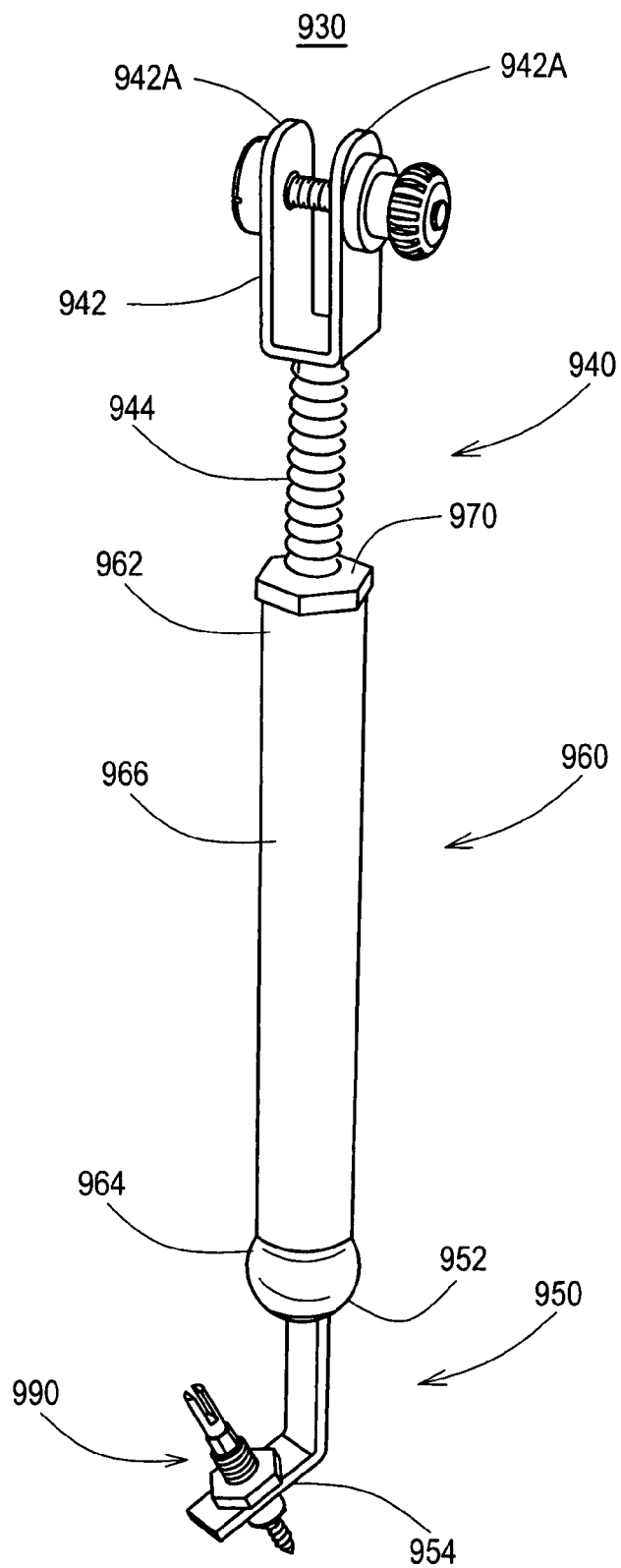
FIGS. 9A and 9B respectively show a perspective view and a cross sectional view of a leg assembly according to one embodiment of the present invention.
Figure 9B:
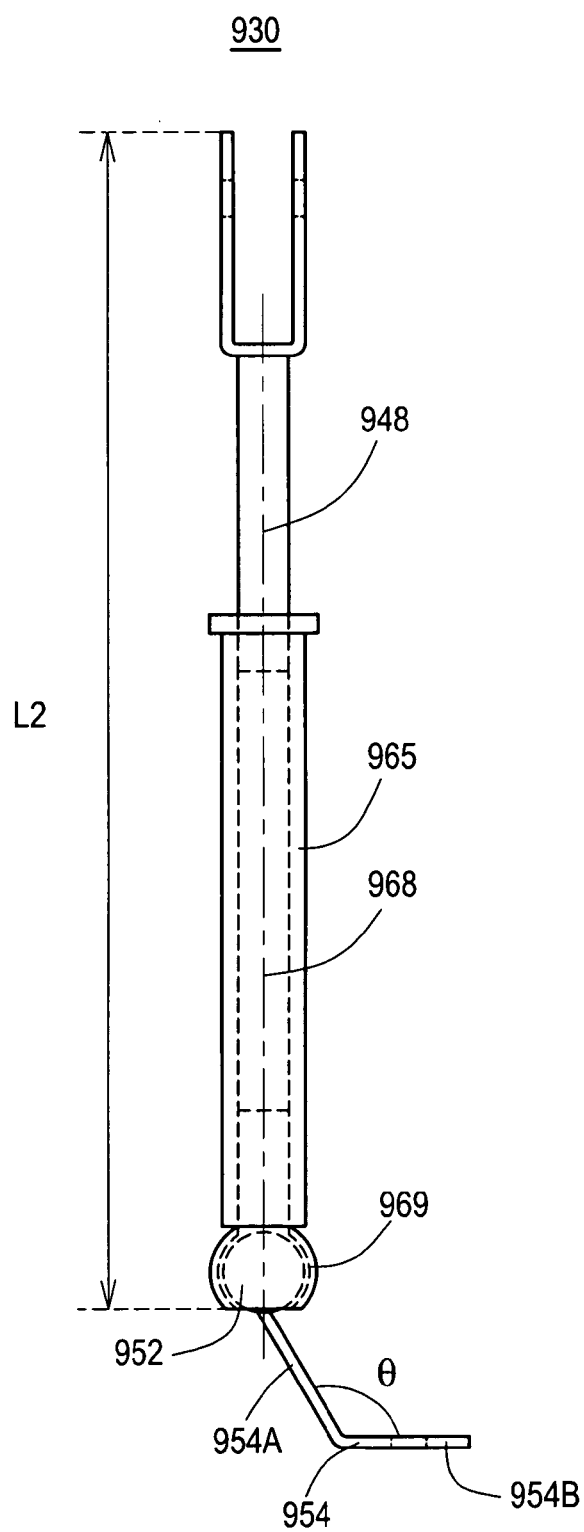

FIGS. 9A and 9B show a leg assembly 930 according to one embodiment of the present invention. The leg assembly 930 has a leg member 940. The leg member 940, same as the first leg member shown in FIGS. 6A and 6B, has a joint portion 942 and an exteriorly threaded shank portion 944 extending from the joint portion 942, and an axis 948 through the joint portion 942 and the exteriorly threaded shank portion 944. The joint portion 942 includes a forked structure having a pair of spaced parallel plates 952A. For this configuration, the leg assembly 930 is connected a ring structure through a one-dimensional motion joint mechanism, as described above. The leg assembly 930 also includes a foot member 950 having a ball joint portion 952 and a foot portion 954 extending from the ball joint portion 952. The foot portion 954 has a first portion 954A proximate to the ball joint portion 952, and a second portion 954B extending from the first portion 954A. The first portion 954A and the second portion 954B define an angle, θ, in a range of about 90-180 degree, preferably at about 120 degree.

The leg assembly 930 further includes a sleeve member 960 having a first end portion 962 and an opposite, second end portion 964 defining a sleeve body 966 therebetween. The sleeve body 966 defines a chamber 965 extending through the first end portion 962 and the second end portion 964 of the sleeve member 960. The sleeve member 960 also has a sleeve axis 968 through the chamber 965. The chamber 965 is formed with an interiorly threaded portion proximate to the first end portion 962 for engaging with the leg member 940, and a housing 969 at the second end portion 964 for accommodating the ball joint 952 of the foot member 950.

As assembled, the ball joint portion 952 of the foot member 950 is received in the housing 969 of the chamber 965 of the sleeve member 960 and the threaded portion 954 of the leg member 940 is received by the threaded portion of the chamber 965 of the sleeve member 950. The axis 948 of the leg member 940 is substantially coincident with the sleeve axis 968. The leg assembly 930 has a leg length, L2, defined between the joint portion 942 of the leg member 940 and the joint portion 952 of the foot member 950. According to the present invention, the leg members 940, the foot member 950 and the sleeve member 960 are adapted such that the leg members 940 is moving back and forth along the axis 968 of the sleeve member 960 as the sleeve member 960 is being rotated around the axis 968, thereby adjusting the leg length L2 of the leg assembly 930. The leg length L2 of the leg assembly 930 can be fixed at a desired length by adjusting a locking nut 970. In the exemplary embodiment, the sleeve member 960 is a cylinder. The foot member 950 is engaged with the sleeve member 960 through a socket-ball joint mechanism. Thus, the foot member 950 can be rotated three-dimensionally around the center of the housing 969 of the chamber 965 of the sleeve member 960.

Practically, the leg assembly 930 is attached onto the skull of a patient by mounting the foot portion 954 of the foot member 950 onto a support member 990 that has a post mounted onto a base secured to the skull of the patient.

Figure 10:
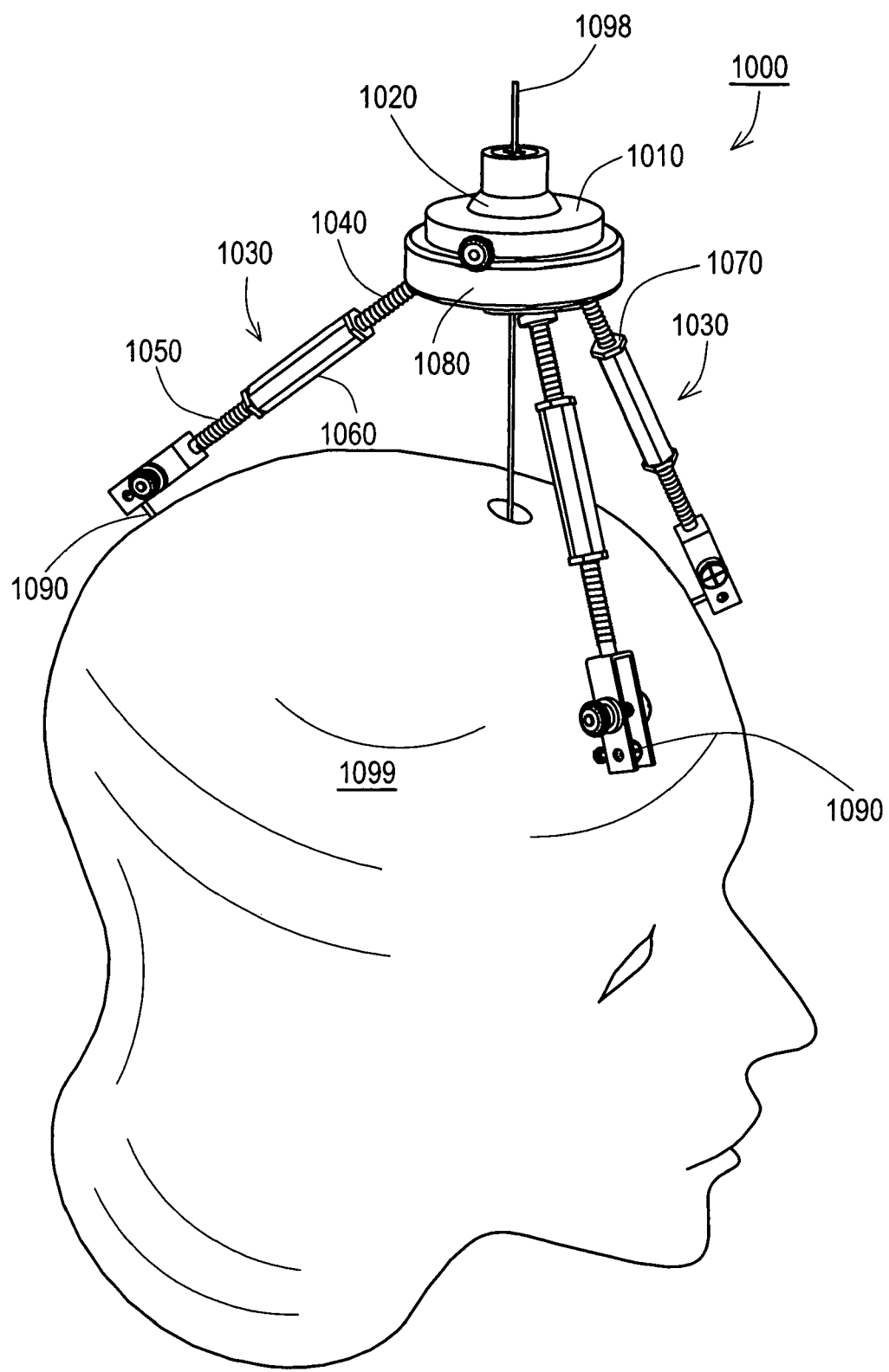
FIG. 10 shows a surgical platform according to one embodiment of the present invention.

Referring to FIG. 10, a surgical platform 1000 according to one embodiment of the present invention includes a ring structure 1010, a ball joint 1020 received in the ring structure 1010, and three leg assemblies 1030 connected to the ring structure 1010. The ring structure 1010 and the ball joint 1020 are structurally same as the ones shown in FIGS. 3A and 3B, and each of the three leg assemblies 1030 is structurally same as the one shown in FIGS. 8A and 8B. In the embodiment, the ball joint portion of the first leg member 1040 of each leg assembly 1030 is connected to the ring structure 1010 through a socket-ball joint mechanism. As disclosed above, the socket-ball joint mechanism enables each leg assembly 1030 to be rotatable three-dimensionally around the socket-ball joint point relative to the ring structure 1010. The surgical platform 1000 is attached onto to a surgical site of interest 1099, by engaging the joint portion of the second leg member 1050 of each leg assembly 1030 with a corresponding support member 1090. A probe 1098 passes through the ball joint 1020 of the surgical platform 1000 and aims at a surgical target point. In operation, the probe 1098 is first pointed at an entry point of surgery by adjusting the ball joint 1020. The ball joint 1020 is then locked by adjusting the locking knob 1080. From the entry point of surgery, a final target of surgery at which the probe 1098 aims is fine tuned by individually adjusting the length of each leg assembly 1030, which is performed by rotating the sleeve member 1060 of the corresponding leg assembly 1030. Once the probe 1098 is brought to the final target point of surgery, each leg assembly 1030 is locked by the locking nuts 1070 during the surgical procedure.

Figure 11:
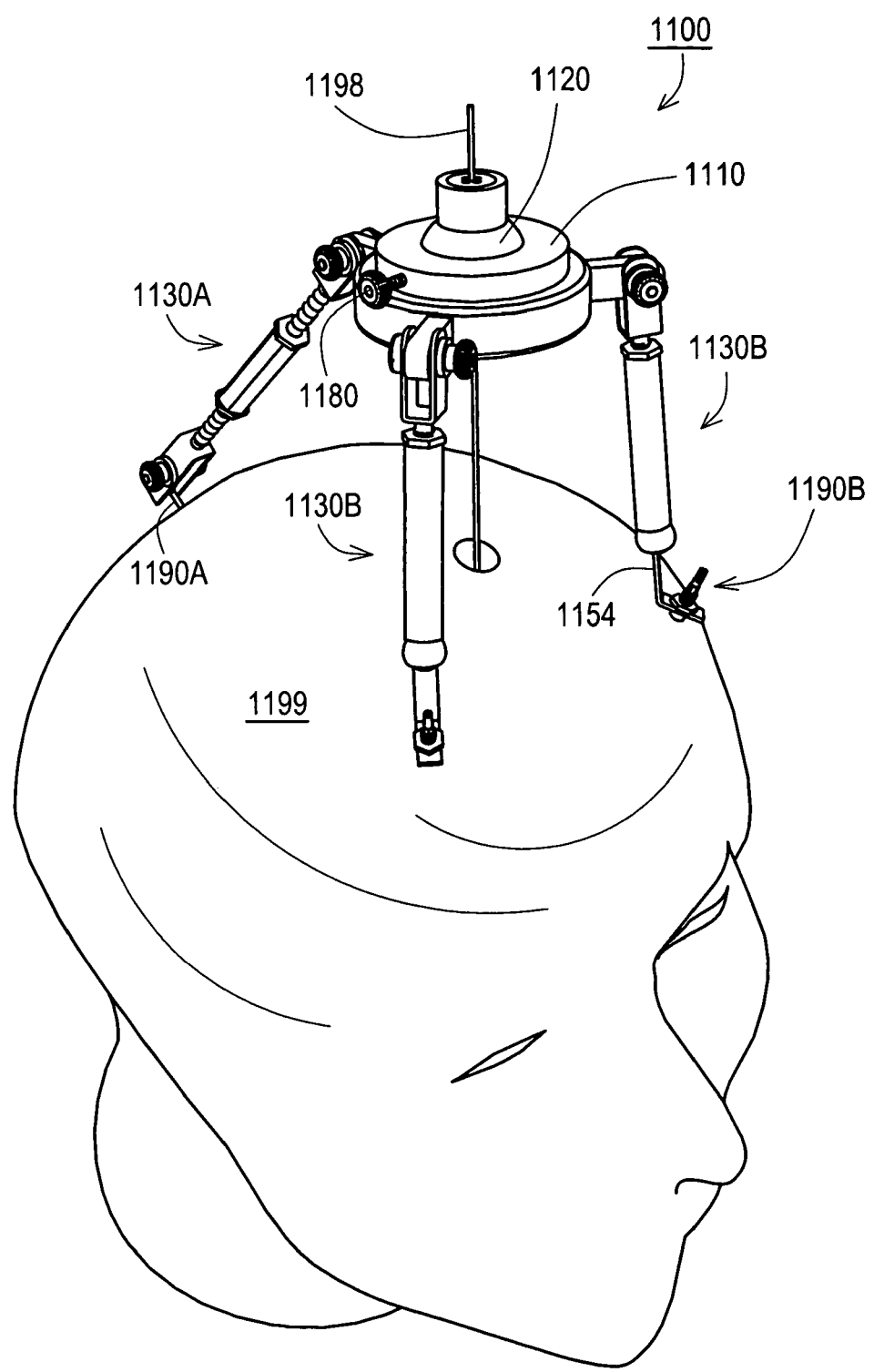
FIG. 11 shows a surgical platform according to another embodiment of the present invention.

FIG. 11 shows another embodiment of a surgical platform 1100 of the present invention. The surgical platform 1100 has a ring structure 1110, a ball joint 1120 housed in the ring structure 1110, and three leg assemblies 1130A and 1130B connected to the ring structure 1110. A probe 1198 passes through the ball joint 1120 of the surgical platform 1100 and aims at a surgical target point. The ring structure 1110 and the ball joint 1120 are structurally same as the ones shown in FIG. 4. The leg assembly 1130A is structurally same as the one shown in FIGS. 6A and 6B, while the leg assembly 1130B is structurally same as the one shown in FIGS. 9A and 9B. In the exemplary embodiment shown in FIG. 11, the joint portion of the first leg member 1140 of each leg assembly 1130A or 1130B is connected to the ring structure 1110 through a one-dimensional motion joint mechanism, which enables each leg assembly 1130A or 1130B to be rotatable one-dimensionally around the joint point.

Figure 12:
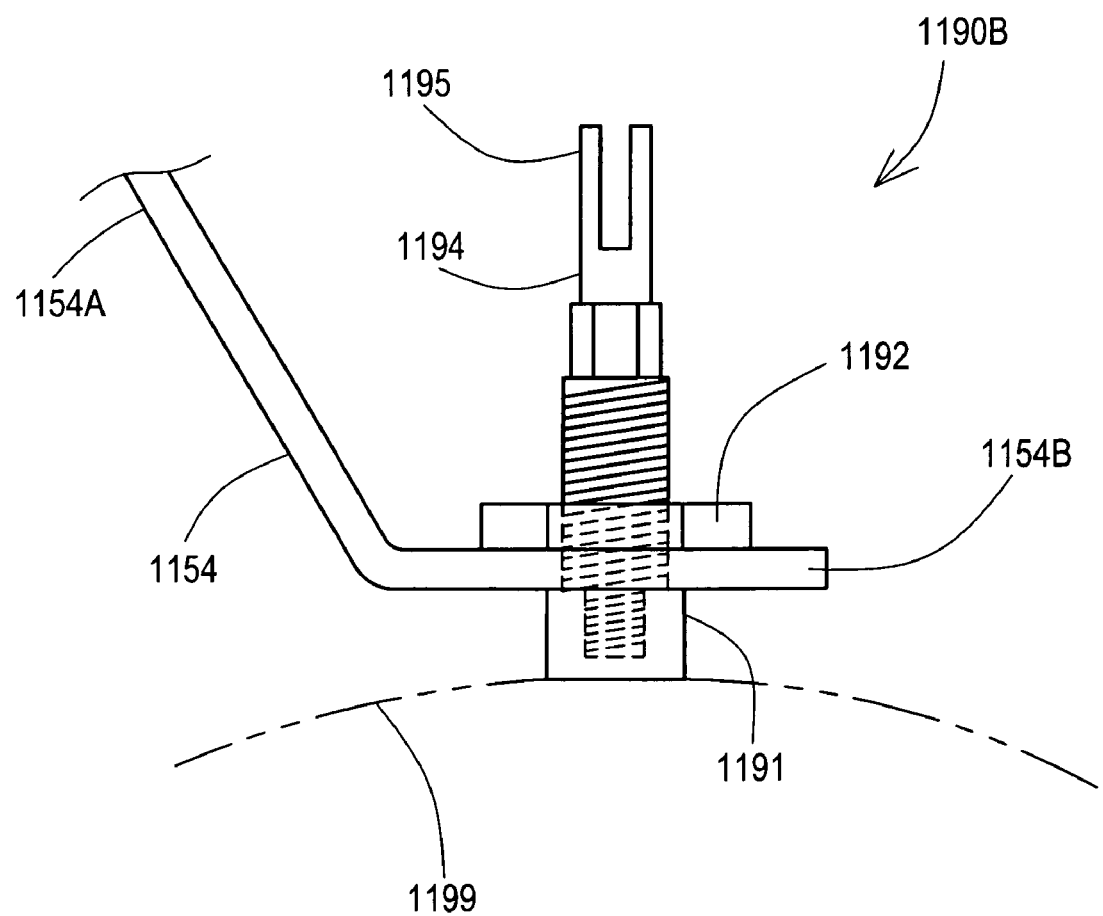
FIG. 12 shows a cross sectional view of a post having a foot member of the surgical platform shown in FIG. 11 mounted therein.

The surgical platform 1100 is attached to a surgical site of interest 1199 in use. For such an embodiment, the joint portion of the second leg member of the leg assembly 1130A is attached to a first type of support member 1190A, while the foot portion 1154 of each leg assembly 1130B is attached to a second type of support member 1190B. The first type of support member 1190A is same as the one shown in FIGS. 1 and 10 and further described below in conjunction with FIG. 13. The second type of support member 1190B, as shown in FIG. 12, includes a base 1191 mounted onto the surgical site of interest 1199 and a post 1194. Practically, the foot portion 1154 of the leg assembly 1130B is placed on the base 1191, and then the post 1194 is mounted onto the base 1191. A top end portion 1195 of the post 1194 accommodates a trackable fiducial marker for an intraoperative tracking system. In this embodiment, during an imaging procedure, a similar post of the same length, made of imageable material such as a plastic, may be provided to support a corresponding imageable fiducial marker at the same position relative to the base 1191. The imaging post at a preoperatively imaging stage may not require a hex nut 1192, because the surgical platform 1100 is not in place during the imaging procedure. During a surgical procedure, a rough adjustment of the leg assembly 1130B of the surgical platform 1100 is first performed so that the foot 1154 stands on the base 1191. Then the post 1194 is placed through the foot 1154 into the base 1191 and tightened to the base 1191 by means of a hex nut 1192. The hex nut 1192 is tightened to clamp the foot 1154 into the base 1191. Then a trackable fiducial marker is attached to the top end portion 1195 of the post 1194. At this stage, an intraoperatively tracking system is used to determine the position of the fiducial marker attached to the post 1194.

Another aspect of the present provides a method of performing a surgical procedure with the invented surgical platform disclosed above. The method in one embodiment includes adjusting the ball joint to bring the working end of the probe onto an initial optimal position in the surgical site of interest at first, and then locking the ball joint against movement relative to the ring structure, by means of a locking knob. The initial optimal position corresponds to an entry point of surgery. From the entry point of surgery, the fine adjustment of the probe trajectory is performed by individually adjusting the lengths of the leg assemblies, which brings the working end of the probe onto a final position from the initial optimal position (the entry point of surgery). The final position corresponds to a final target of surgery. Then, the leg assembles are locked by means of locking nuts so as to remain the leg length unchanged, which ensures the final trajectory of the probe unchanged during the surgical procedure. The procedure can be visualized on a display.

A further aspect of the present invention relates to a fiducial marker. The fiducial marker is adapted as a support member for supporting the surgical platform of the present invention shown in FIGS. 1, 10 and 11. Referring to FIGS. 13A-13E, the fiducial marker 1390 has a ball portion 1392 defining a recess 1391, a shank portion 1394 extending from the ball portion 1392, a threaded portion 1396 extending from the shank portion 1394 for threading into an anatomical structure, and a flange 1395 radially and outwardly extending from the junction of the shank portion 1394 and the threaded portion 1396 and having a first surface 1395A facing the shank portion 1394 and an opposite, second surface 1395B facing the threaded portion 1396. The fiducial marker 1390 also has a serration pattern 1397 formed on the second surface 1395B such that when the fiducial marker 1390 is threaded solidly into an anatomical structure along a first direction, the serration pattern 1397 prevents the fiducial marker 1390 from moving along a second direction opposite to the first direction.

Figure 13A:
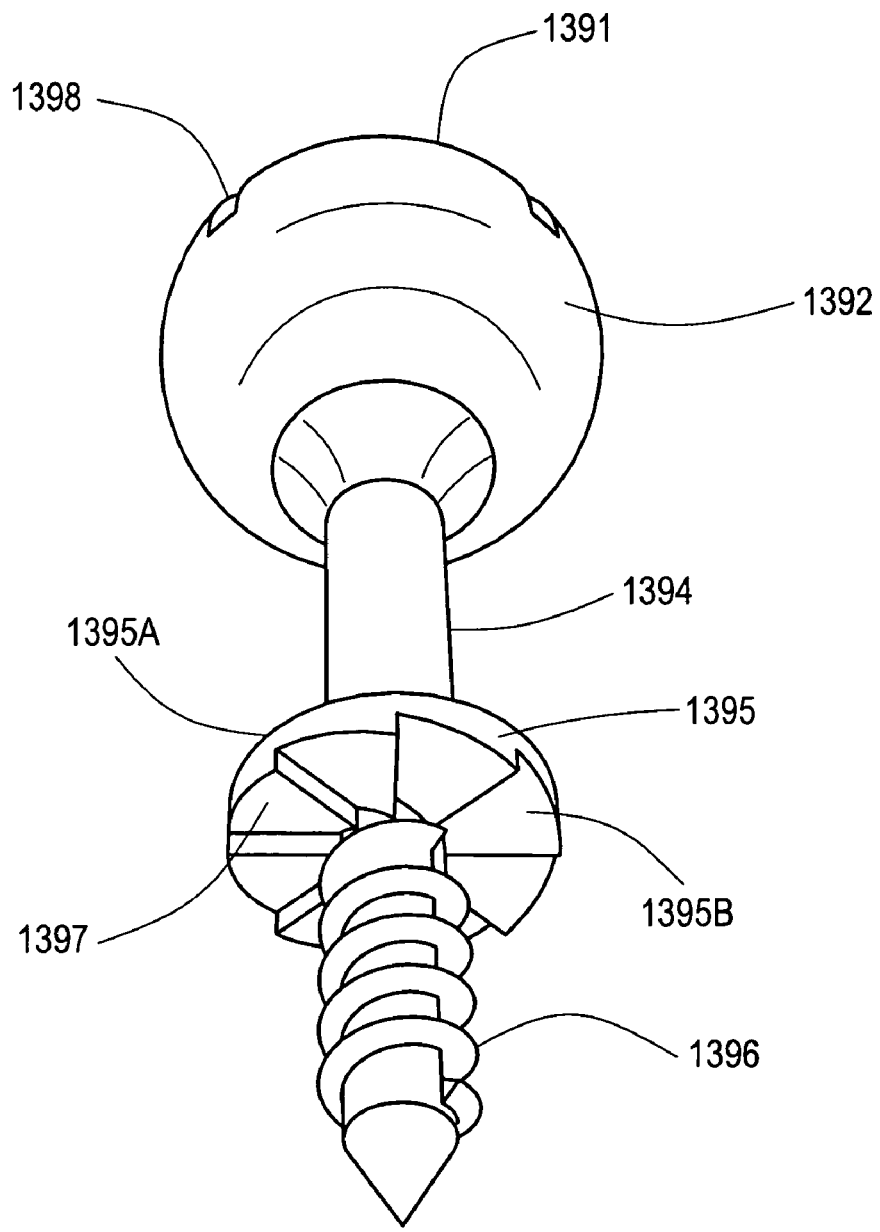
FIGS. 13A-13E respectively show a perspective view, cross sectional views, and top views of a fiducial marker according to different embodiments of the present invention.
Figure 13B:
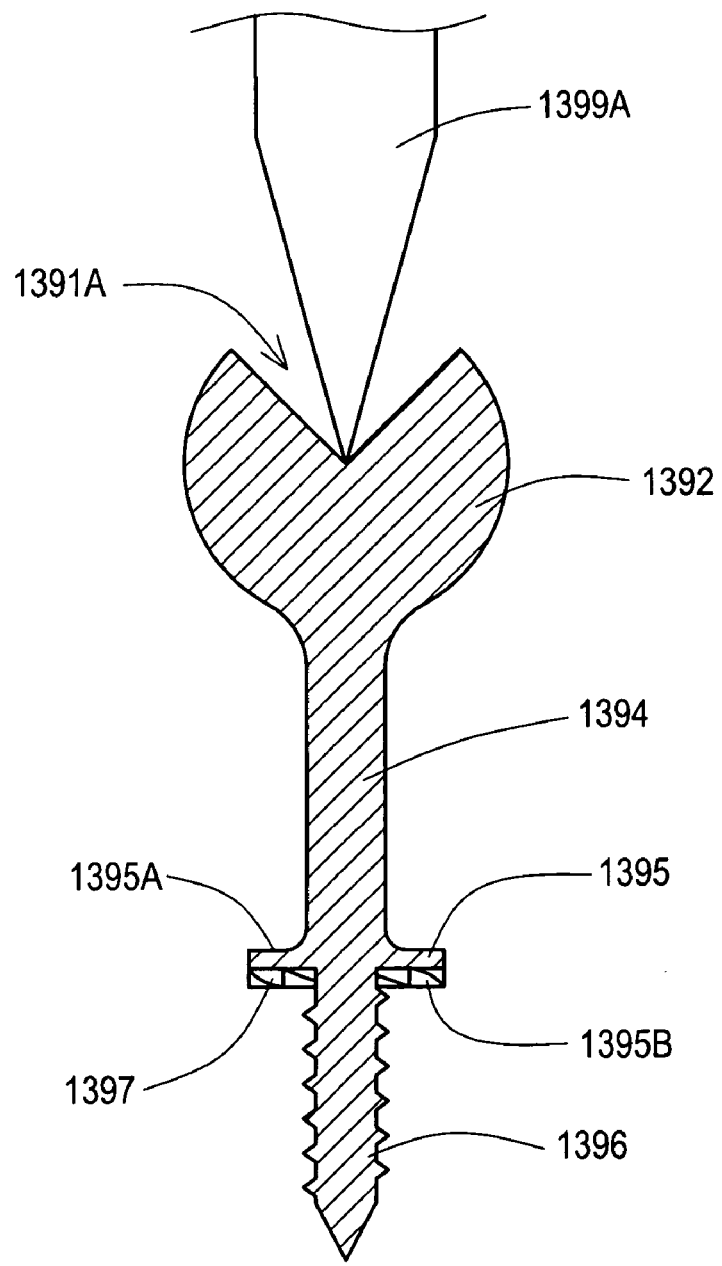
Figure 13C:
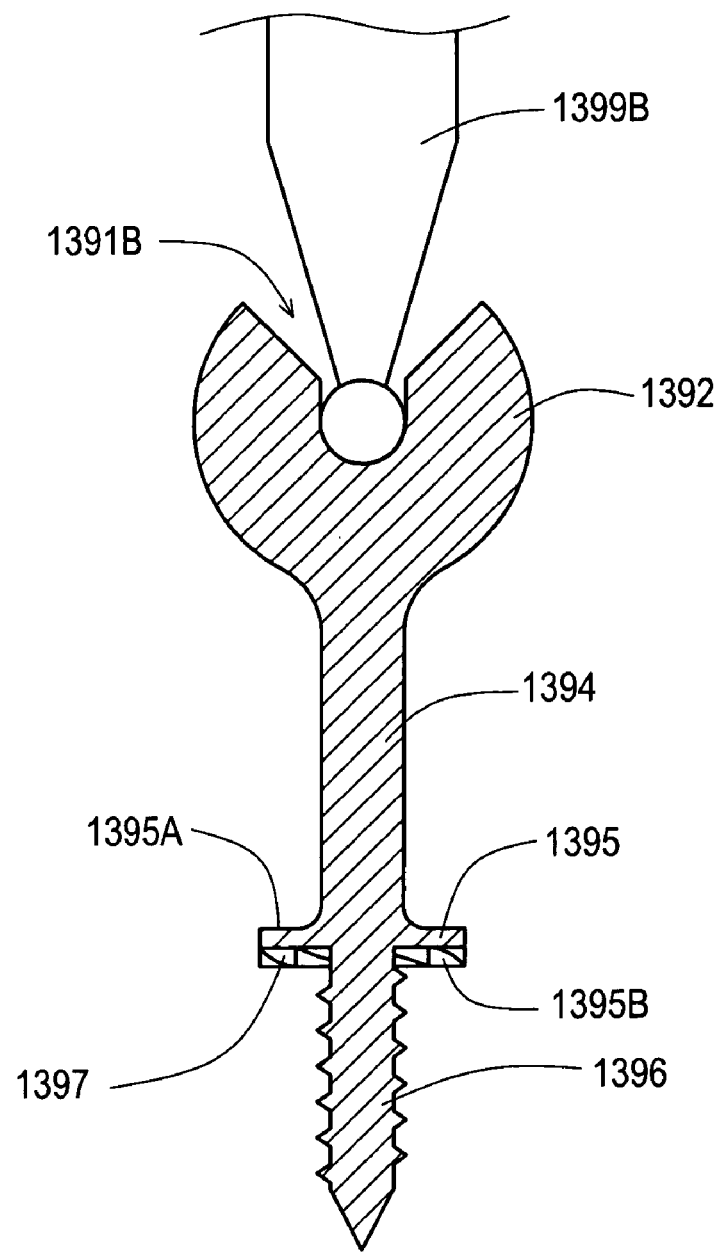

The recess 1391 is adapted for accommodating a working end of a registration probe. For example, as shown in FIG. 13B, the recess 1391A is formed in the form of a cone, and is used to accommodate a registration probe 1399A having a needle-type working end. FIG. 13C shows a recess 1391B in the form of a cone having a hollow hemisphere formed at the apex of the cone, which is used to accommodate a registration probe 1399B having a ball-type working end. The registration probe 1399A (1399B) is operably rotated around the apex of the recess 1391A (1391B) for target localization during the surgical procedure.

Figure 13D:
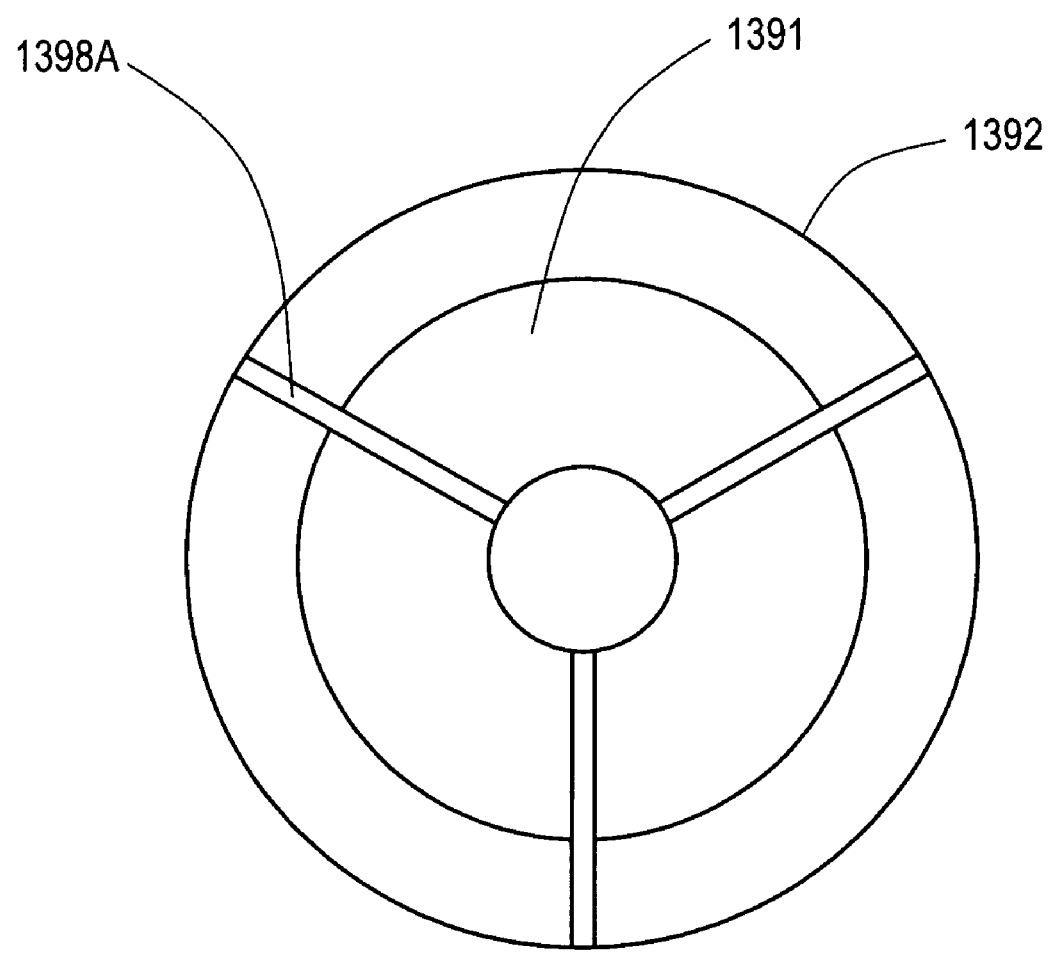
Figure 13E:
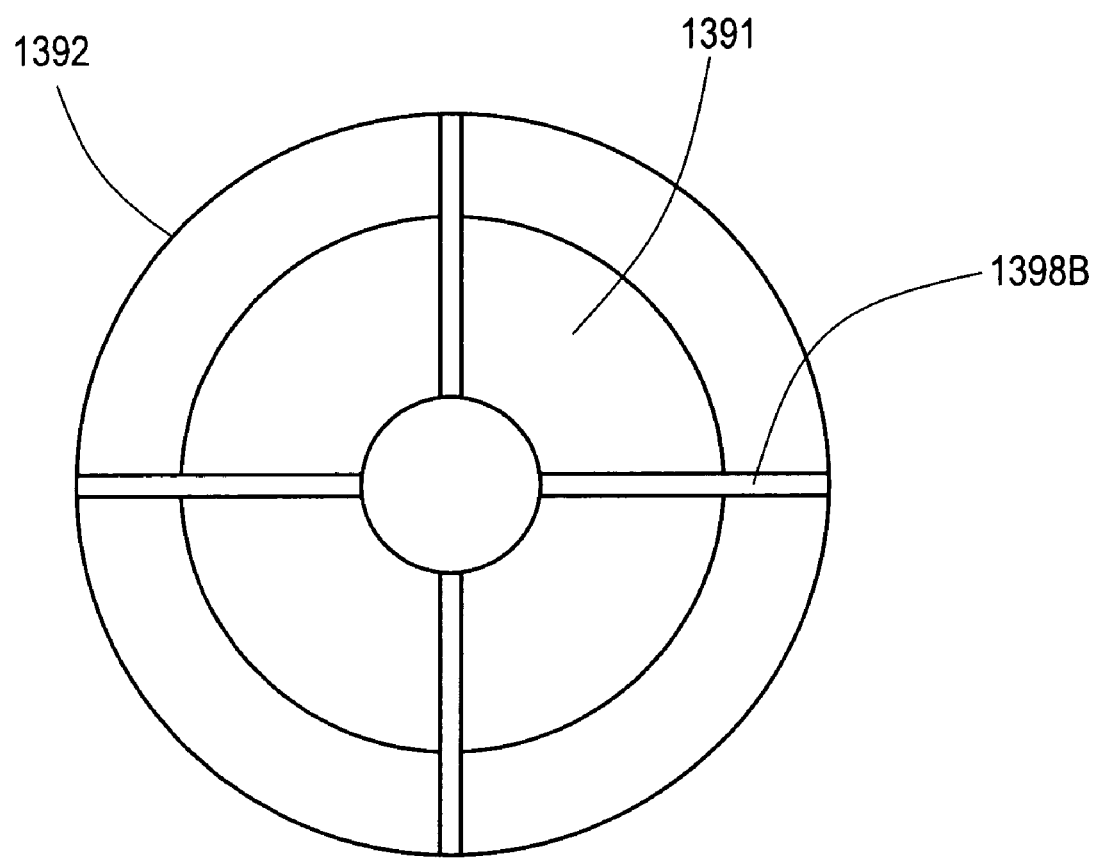

Additionally, the fiducial marker 1390 has a pattern of grooves 1398 configured to receive a screw driver for applying a torque to the fiducial marker 1390 to thread it into an anatomical structure. FIGS. 13D and 13E show two different patterns of grooves 1398A and 1398B, respectively. The pattern of groove 1398A is for a triangle-type screw driver, while the pattern of groove 1398B is for a Phillip-type screw driver.

According to the present invention, in addition to support a corresponding leg assembly of a surgical platform, the fiducial marker 1390 is also adapted for target registration and localization. Therefore the fiducial marker 1390 is preferably made of material that is imageable and trackable preoperatively, intraoperatively and/or postoperatively.

The present invention, among other things, discloses an adjustable surgical platform that is more easily adjustable, yet more stable and easy to lock to the target of surgery, and that provides ample space for access. The surgical platform is re-usable or disposable.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A surgical platform, comprising:
   a. a ring structure having a first end portion, and an opposite, second end portion, and a body portion therebetween, wherein the body portion defines a housing extending between the first and second end portions;
   b. a ball joint configured to be received in the housing of the ring structure and be rotatable around its center, wherein the ball joint defines at least one bore for accommodating a probe therethrough;
   c. a plurality of leg assemblies, each leg assembly comprising:
      (i). a first leg member having a joint portion detachably connected to the ring structure, an exteriorly threaded shank portion extending away from the joint portion, and an axis through the joint portion and the exteriorly threaded shank portion;
      (ii). a second leg member having a joint portion, an exteriorly threaded shank portion extending away from the joint portion, and an axis through the joint portion and the exteriorly threaded shank portion; and
      (iii). a sleeve member having a first end portion and an opposite, second end portion defining a sleeve body therebetween, and an axis through the sleeve body, wherein the sleeve body defines a chamber interiorly threaded for engaging with the first and second leg members, respectively,
      wherein as assembled, the threaded shank portions of the first and second leg members are received in the chamber through the first and second end portions of the sleeve member, respectively, such that the axes of the first and second leg members are substantially coincident with the axis of the sleeve member, and the first and second leg members are movable back and forth along the axis of the sleeve member when the sleeve member is being rotated around its axis, thereby adjusting a leg length defined between the joint portion of the first leg member and the joint portion of the second leg member; and
   d. a plurality of support members detachably mountable to an anatomical structure, each support members having a ball portion,
      wherein the joint portion of the second leg member of each leg assembly comprises a forked structure having a pair of spaced plates and a securing member adjustably mounted onto the pair of spaced plates, each plate defining a hole for accommodating the ball portion of a support member to form a socket-ball joint mechanism therein, and wherein as assembled, the pair of spaced plates of the forked structure of the second leg member of each leg assembly is connected to the ball portion of a corresponding support member through the socket-ball joint mechanism and secured thereto by adjusting the securing member such that the second leg member of the leg assembly is rotatable around the center of the ball portion of the corresponding support member.

2. The surgical platform of claim 1, further comprising a locking knob located at the body portion of the ring structure and adapted for adjustably locking the ball joint against movement relative to the ring structure.

3. The surgical platform of claim 1, wherein the joint portion of the first leg member of each leg assembly is connected to the ring structure through a socket-ball joint mechanism.

4. The surgical platform of claim 3, wherein the ring structure has a plurality of sockets formed in the second end portion, wherein the joint portion of the first leg member of each leg assembly comprises a ball joint, and wherein as assembled, the ball joint of the first leg member of each leg assembly is received by a corresponding socket of the ring structure such that the leg assembly is rotatable around the center of the ball joint.

5. The surgical platform of claim 1, wherein the ring structure has a first plurality of tabs extending radially and outward from the body portion of the ring structure, each tab defining a hole therein, and a second plurality of sockets formed at the second end portion.

6. The surgical platform of claim 1, wherein each support member comprises a trackable fiducial marker.

7. The surgical platform of claim 1, wherein the plurality of leg assemblies are equiangularly apart from each other.

8. The surgical platform of claim 1 made from one or more metallic materials or from one or more plastic materials.

9. A surgical platform, comprising:
   a. a ring structure having a first end portion, an opposite, second end portion, and a body portion therebetween, wherein the body portion defines a housing extending between the first and second end portions;
   b. a ball joint configured to be received in the housing of the ring structure and be rotatable around the center of the ball joint, wherein the ball joint defines at least one bore for accommodating a probe therethrough;
   c. a plurality of leg assemblies connected to the ring structure, each leg assembly comprising:
      (i). a first leg member and a second leg member, each of the first and second leg members having a joint portion and a shank portion extending from the joint portion, respectively; and
      (ii). a sleeve member having a first end portion and an opposite, second end portion defining a sleeve body therebetween, and an axis through sleeve body, wherein the sleeve body defines a chamber,
      wherein as assembled, the shank portions of the first and second leg members are received by the chamber through the first and second end portions of the sleeve member, respectively, such that the first and second leg members and the sleeve member are coaxial, and at least one of the first and second leg members is movable back and forth along the axis of the sleeve member when the sleeve member is rotated around the axis, thereby adjusting a leg length defined between the joint portion of the first leg member and the joint portion of the second leg member; and
   d. a plurality of support members detachably mountable to an anatomical structure, each support members having a ball portion,
   wherein the joint portion of the second leg member of each leg assembly comprises a forked structure having a pair of spaced plates and a securing member adjustably mounted onto the pair of spaced plates, each plate defining a hole for accommodating the ball portion of a support member to form a socket-ball joint mechanism therein, and wherein as assembled, the pair of spaced plates of the forked structure of the second leg member of each leg assembly is connected to the ball portion of a corresponding support member through the socket-ball joint mechanism and secured thereto by adjusting the securing member such that the second leg member of the leg assembly is rotatable around the center of the ball portion of the corresponding support member.

10. The surgical platform of claim 9, further comprising a locking knob located at the body portion of the ring structure and adapted for adjustably locking the ball joint against movement relative to the ring structure.

11. The surgical platform of claim 9, wherein at least one of the shank portions of the first and second leg member is exteriorly threaded, and wherein the chamber of the sleeve member has at least one interiorly threaded portion proximate to one of the first and second ends of the sleeve member for engaging with the at least one of the shank portions of the first and second leg member.

12. The surgical platform of claim 9, wherein the joint portion of the first leg member of each leg assembly is connected to the ring structure through a motion joint mechanism.

13. The surgical platform of claim 9, wherein the joint portion of the first leg member of each leg assembly is connected to the ring structure through a socket-ball joint mechanism.

14. The surgical platform of claim 9, wherein each support member comprises a trackable fiducial marker.

15. The surgical platform of claim 9 made from one or more metallic materials or from one or more plastic materials.

* * * * *

UNITED STATES PATENT AND TRADEMARK OFFICE
CERTIFICATE OF CORRECTION

| | | |
|---|---|---|
| PATENT NO. | : 7,794,469 B2 | Page 1 of 1 |
| APPLICATION NO. | : 11/594700 | |
| DATED | : September 14, 2010 | |
| INVENTOR(S) | : Changquing C. Kao et al. | |

It is certified that error appears in the above-identified patent and that said Letters Patent is hereby corrected as shown below:

In Column 1, Lines 25 to 31 delete:

"STATEMENT OF FEDERALLY SPONSORED RESEARCH
This invention was made in part with U.S. Government support under Grant R21CA133477, awarded by the National Institute of Health. The U.S. Government has certain rights in this invention."

Signed and Sealed this

Eleventh Day of January, 2011

David J. Kappos
*Director of the United States Patent and Trademark Office*